(12) United States Patent
Imura

(10) Patent No.: US 7,675,620 B2
(45) Date of Patent: Mar. 9, 2010

(54) OPTICAL PROPERTY MEASURING METHOD AND OPTICAL PROPERTY MEASURING APPARATUS

(75) Inventor: Kenji Imura, Toyohashi (JP)

(73) Assignee: Konica Minolta Sensing, Inc., Sakai-shi (JP)

(*) Notice: Subject to any disclaimer, the term of this patent is extended or adjusted under 35 U.S.C. 154(b) by 291 days.

(21) Appl. No.: 11/999,273

(22) Filed: Dec. 5, 2007

(65) Prior Publication Data
US 2008/0137086 A1  Jun. 12, 2008

(30) Foreign Application Priority Data
Dec. 8, 2006 (JP) ............... 2006-331756

(51) Int. Cl.
*G01J 3/00* (2006.01)
*G01J 3/46* (2006.01)

(52) U.S. Cl. ............ 356/402; 356/300; 356/319; 356/72

(58) Field of Classification Search ........ 356/300, 356/319, 326, 402, 72
See application file for complete search history.

(56) References Cited

U.S. PATENT DOCUMENTS

| | | | | |
|---|---|---|---|---|
| 4,635,213 A | * | 1/1987 | Murata et al. | 382/111 |
| 5,636,015 A | | 6/1997 | Imura et al. | 356/72 |
| 6,020,959 A | * | 2/2000 | Imura | 356/319 |
| 6,535,278 B1 | * | 3/2003 | Imura | 356/73 |
| 7,466,417 B2 | * | 12/2008 | Ehbets et al. | 356/402 |

FOREIGN PATENT DOCUMENTS

| JP | 08-313349 | | 11/1996 |
|---|---|---|---|
| JP | 2006157107 A | * | 6/2006 |

* cited by examiner

*Primary Examiner*—L. G Lauchman
(74) *Attorney, Agent, or Firm*—Sidley Austin LLP

(57) ABSTRACT

In an optical property measuring method and an optical property measuring apparatus, a spectral transmittance characteristic of a reference colored layer prepared as a reference is corrected based on a measured spectral reflection characteristic of a colored layer, and the spectral reflection characteristic of the reference colored layer. With this arrangement, information on the measured spectral transmittance characteristic of the colored layer can be obtained with sufficient precision in conformity with a printing condition of a sample to be measured. Thus, colorimetry of a printed color of a fluorescent sample i.e. a colored surface on a fluorescent substrate can be accurately performed by using the corrected spectral transmittance characteristic of the reference colored layer.

13 Claims, 15 Drawing Sheets

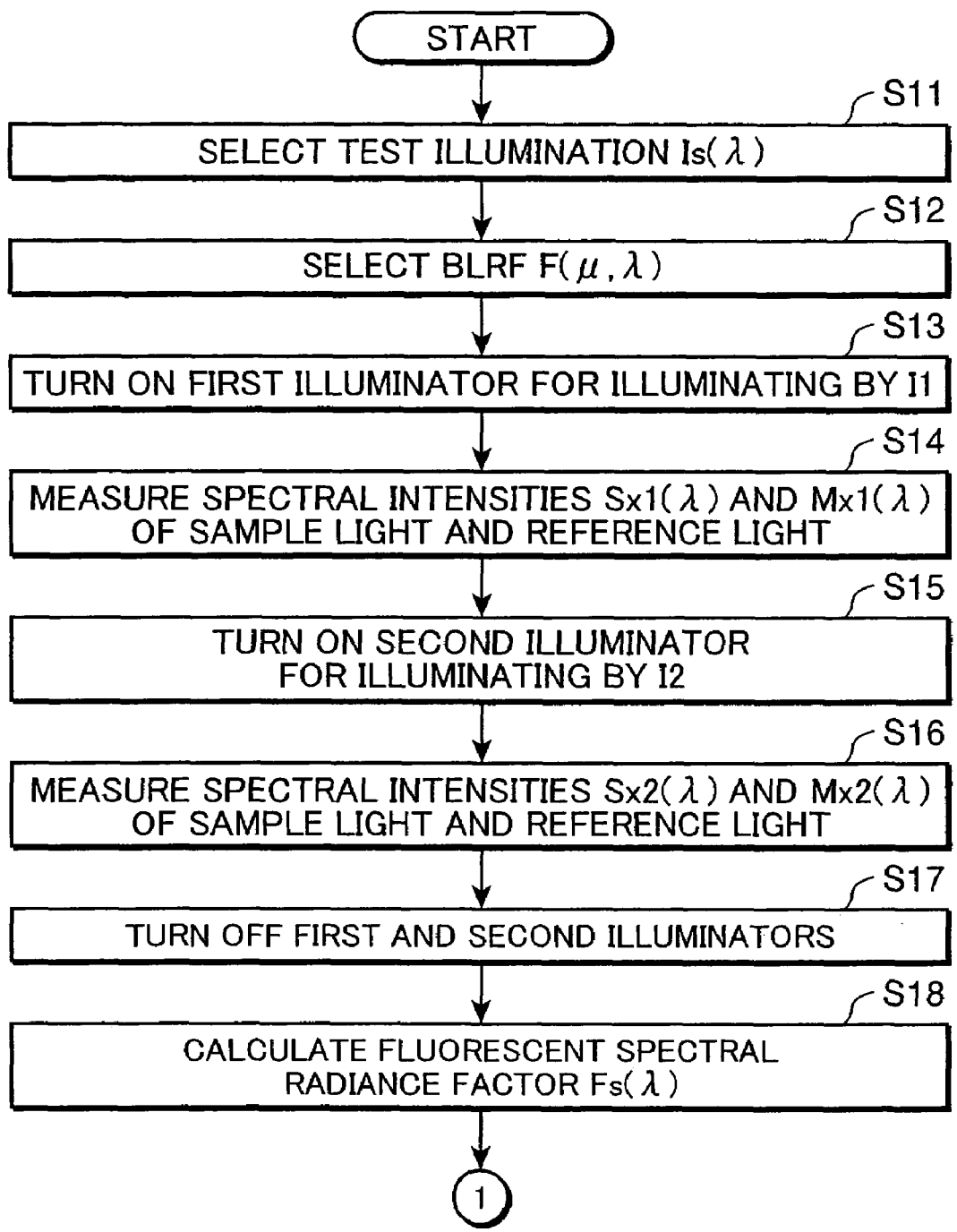

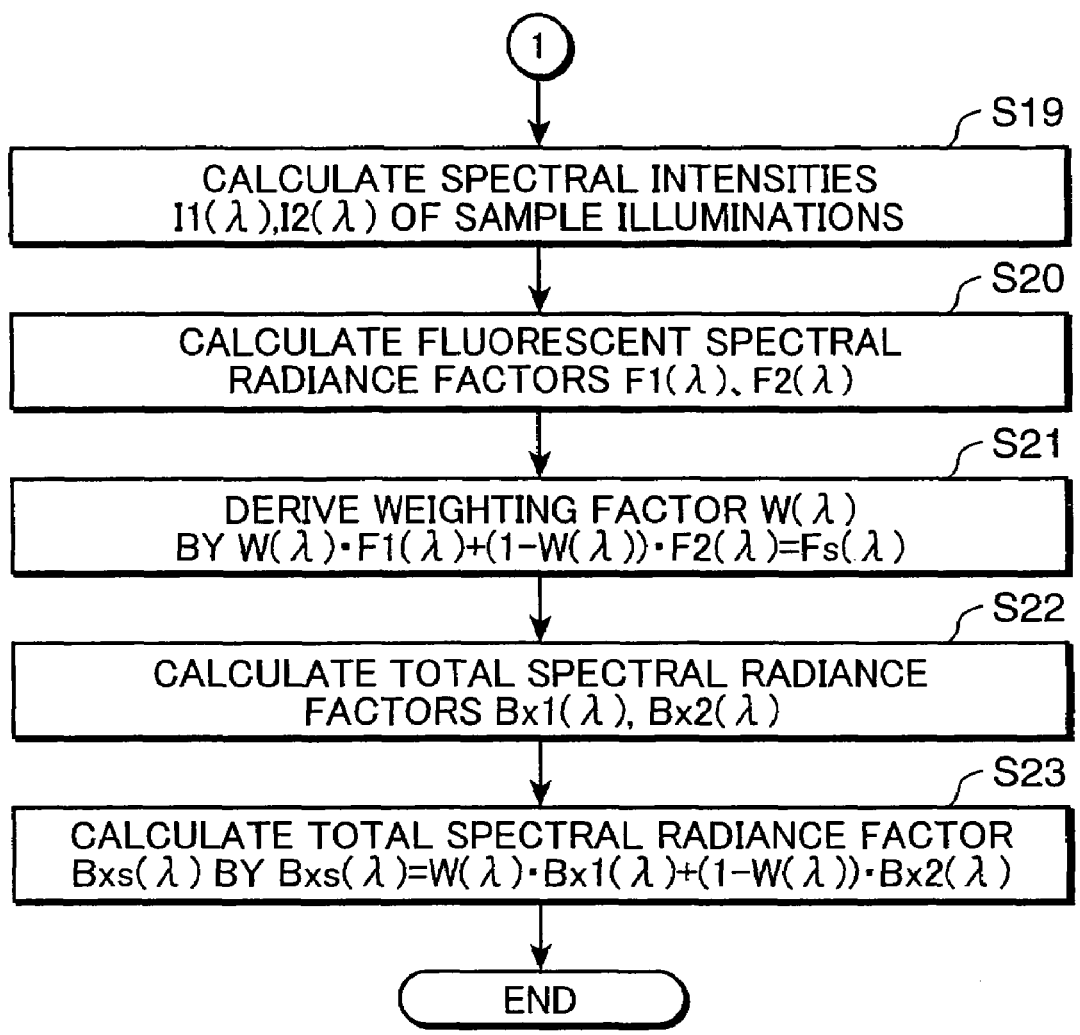

OPTICAL PROPERTY MEASURING METHOD AND OPTICAL PROPERTY MEASURING APPARATUS

This application is based on Japanese Patent Application No. 2006-331756 filed on Dec. 8, 2006, the contents of which are hereby incorporated by reference.

BACKGROUND OF THE INVENTION

1. Field of the Invention

The present invention relates to an optical property measuring method and an optical property measuring apparatus for measuring an optical property of a colored surface on a fluorescent substrate.

2. Description of the Related Art

Today, paper and fabrics are often treated by FWA (Fluorescent Whitening Additives). It is extremely difficult to evaluate the color of a colored surface of these products or an article using these products as a substrate, without considering an effect of fluorescent light. In view of the above, there is a demand for improvement in colorimetry of a colored surface of the FWA treated paper or fabrics, or the article using these products as the substrate, considering an effect of fluorescent light.

Generally, a visible property of a reflecting sample is expressed relatively to the perfect white, namely, based on the total spectral radiance factor $B(\lambda)$. The total spectral radiance factor $B(\lambda)$ is the ratio of light emitted from the sample to that from the perfect reflecting diffuser in the identical illuminating and receiving conditions at each wavelength $\lambda$.

A color of fluoresced light is observed as a light source color alone. In case of a sample containing a fluorescent substance (hereinafter, called as "fluorescent sample"), however, the fluoresced light is added to the reflected light, and the color thereof is observed as an objective color. That is, the light emitted from the fluorescent sample is the sum of the reflected light and the fluoresced light, and accordingly, the total spectral radiance factor $B(\lambda)$ of the fluorescent sample is also given as the sum of reflection spectral radiance factor $R(\lambda)$ and the fluorescent spectral radiance factor $F(\lambda)$ which are the ratios of light reflected and fluoresced from the sample respectively to the light from the perfect reflecting diffuser in the identical illuminating and receiving conditions as expressed by Equation (1).

$$B(\lambda)=R(\lambda)+F(\lambda) \tag{1}$$

Since the above-mentioned perfect reflecting diffuser has no fluorescence, and the reflectivity thereof has no dependence on the wavelength of illumination light, the above-mentioned total spectral radiance factor $B(\lambda)$, reflection spectral radiance factor $R(\lambda)$ and fluorescent spectral radiance factor $F(\lambda)$ are equivalent to the ratios of the light emitted, reflected and fluoresced from the sample respectively to the illumination light with a suitable proportional coefficient. An object of the colorimetry is to obtain a measurement value analogous to visual observation. The color of a fluorescent sample is observed as an objective color, and accordingly is related to the total spectral radiance factor $B(\lambda)$, from which the colorimetric values are derived.

CIE (International Committee of Illumination) defines spectral intensity distributions of several standard illuminations for colorimetry such as Illuminant D65, D50, D75 (daylight), Illuminant A(incandescent lamp), Illuminant F11, and Illuminant C. For the evaluation of fluorescent samples, Illuminant D65 is generally used. The spectral excitation-fluorescence characteristics of a fluorescent sample or a fluorescent substrate illuminated with illumination light is expressed by the Bi-spectral Luminescent Radiance Factor (referred to as "BLRF" hereinafter) $F(\mu,\lambda)$ which is the matrix data showing the intensity of the fluoresced light at wavelength $\lambda$ excited by excitation light i.e. incident light of wavelength $\mu$ for illuminating the fluorescent sample surface with a unit intensity i.e. by monochromatic light of a unit intensity at wavelength $\mu$.

An example of the above-mentioned matrix data is shown in FIG. 8, wherein the cross-section along the fluorescence wavelength $\lambda$ expresses the spectral excitation efficiency for fluorescing at wavelength $\lambda$ while the cross-section along the excitation wavelength expresses the spectral intensity of fluoresced light excited at wavelength $\mu$. Accordingly, a sample containing a fluorescent substance of the bi-spectral luminescent radiance factor $F(\mu,\lambda)$ has the fluorescent spectral radiance factor $F(\lambda)$ expressed by Equation (2), where the proportional coefficient is neglected, when illuminated by illumination I of the spectral intensity $I(\lambda)$.

$$F(\lambda)=\int F(\mu,\mu)\cdot I(\mu)d\mu/I(\lambda) \tag{2}$$

That is, $F(\lambda)$ is obtained as the ratio of convolution of the spectral intensity $I(\mu)$ of illumination I and the bi-spectral luminescent radiance factor $F(\mu,\lambda)$ to $I(\lambda)$.

As indicated by Equation (2), the fluorescent spectral radiance factor $F(\lambda)$ depends on the spectral intensity $I(\mu)$ of the illumination I. Accordingly, the total spectral radiance factor $B(\lambda)$, which is the sum of the reflection spectral radiance factor $R(\lambda)$ which itself does not depend on the spectral intensity $I(\mu)$ of the illumination I and the fluorescent spectral radiance factor $F(\lambda)$, and the colorimetric values derived therefrom also depend on $I(\mu)$.

As the result, the spectral intensity $I(\mu)$ of illumination light (referred to as "test illumination" hereinafter) need to be specified when evaluating the optical property of a fluorescent sample and for the accurate measurement, the spectral intensity $I(\mu)$ of illumination light of a measuring apparatus need to be the same as that of the specified test illumination. However, it is difficult and expensive to realize such an illumination of the same spectral intensity as that of the standard illuminant D65 or C generally used as the test illumination.

Alternatively, the total spectral radiance factor $B(\lambda)$ or the fluorescent spectral radiance factor $F(\lambda)$ can be calculated using Equation (2) with the measured bi-spectral luminescent radiance factor $F(\mu,\lambda)$ or bi-spectral radiance factor $B(\mu,\lambda)$ of the sample and the spectral intensity $I(\mu)$ of the test illumination given as numerical data. Here, similarly to the bi-spectral luminescent radiance factor $F(\mu,\lambda)$, the bi-spectral radiance factor $B(\mu,\lambda)$ is the matrix data showing the intensity of the total emission which is the sum of the fluoresced light at wavelength $\lambda$ excited by monochromatic light of a unit intensity at wavelength $\mu$ and the reflected light. The total spectral radiance factor $B(\mu,\lambda)$ is obtained as the ratio of the convolution of the spectral intensity $I(\mu)$ of the illumination I and the bi-spectral radiance factor $B(\mu,\lambda)$ to $I(\lambda)$.

$$B(\lambda)=\int B(\mu,\lambda)\cdot I(\mu)d\mu/I(\lambda) \tag{2-1}$$

However, since the measurement of the bi-spectral luminescent radiance factor $F(\mu,\lambda)$ or the bi-spectral radiance factor $B(\mu,\lambda)$ requires a complicated and expensive bi-spectro-fluorometer e.g. a double monochromator comprising two spectral units, one for illumination and the other for receiving, and long time for measurement, this method is not practical. Quality controls of products treated by FWA such as paper are performed generally using either of the following two simplified methods.

(Gaertner and Griesser's Method)

As shown in FIG. 10, a fluorescent sample 601 is placed at a sample aperture 603 of an integrating sphere 602 of a measuring apparatus 600 for measuring an optical property. A light source 604 such as a xenon flash lamp contains a sufficient UV component, and a light flux 605 from the light source 604 passes through the aperture and enters into the integrating sphere 602. A UV cut filter 605 is inserted so as to partially block the optical path of the light flux 605, and a part of the light flux 605 which passes through the UV cut filter 606 has the UV component eliminated. The degree of insertion of the UV cut filter 606 is adjustable so as to allow adjustment of the UV intensity in the illumination light. The light flux 605 partly passing through the UV cut filter 606 and entering into the integrating sphere 602 undergoes diffuse reflection within the sphere 602 and forms diffuse light which illuminates the fluorescent sample 601. Radiant light 607 emitted in a predetermined direction from the illuminated surface passes through the observation aperture and enters a sample spectral unit 608 for detecting the spectral intensity $Sx(\lambda)$. Similarly, a light flux 609 having substantially the same intensity as the illumination light of the fluorescent sample 601 enters a monitoring optical fiber 610 so as to be directed to a monitoring spectral unit 611 for detecting the spectral intensity $Mx(\lambda)$. A controller 612 calculates the total spectral radiance factor $Bx(\lambda)$ based on information on the spectral intensities $Sx(\lambda)$ and $Mx(\lambda)$ detected by the spectral units 608 and 611. (see FIG. 4 of Japanese Unexamined Patent Publication No. Hei 8-313349 corresponding to U.S. Pat. No. 5,636,015).

A fluorescent standard containing a fluorescent substance with excitation-fluorescence characteristics, namely, the bi-spectral luminescent radiance factor $F(\mu,\lambda)$ substantially identical or similar to that of the sample to be measured and given a colorimetric value such as CIE whiteness under the specific test illumination is used to determine the degree of insertion of the UV cut filter 606. The fluorescent standard is measured by the measuring apparatus 600, and the UV intensity is corrected by adjusting the degree of insertion of the UV cut filter 606 so as to match the value of CIE whiteness calculated from the obtained total spectral radiance factor $Bx(\lambda)$ to the CIE whiteness given to the fluorescent standard.

Gaertner and Griesser's method is mechanically complicated and unreliable, and also requires complicated and time-consuming operation, that is, measurements and movements of the UV cut filter need to be repeated until the measured calorimetric value, CIE whiteness, for example, agrees the given value. This method results in the single specific colorimetric value, CIE value, in this case, compatible to that under a specific test illumination. However, in principle, the multiple calorimetric values, the CIE whiteness and Tint value, for example, or the total spectral radiance factor $Bx(\lambda)$ are not compatible simultaneously.

(Method of U.S. Pat. No. 5,636,015)

As described above, Gaertner and Griesser's method modifies the UV content in the illumination first and modifies the total spectral radiance factor $Bx(\lambda)$ as the result. This method numerically synthesizes the total spectral radiance factor $Bx(\lambda)$ first and synthesizes the illumination of the spectral intensity necessary for $Bx(\lambda)$ as the result. In U.S. Pat. No. 5,636,015, as shown in FIG. 11, an integrating sphere 702 of a measuring apparatus 700 is provided with a first illuminator 704 for emitting a light flux 703 containing a UV component and a second illuminator 706 for emitting a light flux 705 containing no UV component. The measuring apparatus 700 is further provided with a first spectral unit 709 for detecting the spectral intensity of emitted light 708 from a fluorescent sample 701 placed at a sample aperture 707 and a second spectral unit 712 for detecting the spectral intensity of a light flux 710 of the illumination through the optical fiber 711, and a control unit 713.

In the measuring apparatus 700, the fluorescent sample 701 is illuminated by the first and second illuminators 704 and 706 consecutively, and the spectral intensities $Sx1(\lambda)$ and $Sx2(\lambda)$ of emitted light from the sample, and the spectral intensities $Mx1(\lambda)$ and $Mx2(\lambda)$ of the illumination light are respectively detected. The total spectral radiance factors $Bx1(\lambda)$ and $Bx2(\lambda)$ corresponding to the illuminations by the first and second illuminators 704 and 706 are obtained from $Sx1(\lambda)$, $Sx2(\lambda)$, $Mx1(\lambda)$, and $Mx2(\lambda)$ and thus, the total spectral radiance factor $Bxc(\lambda)$ is synthesized by linearly combining $Bx1(\lambda)$ and $Bx2(\lambda)$ with the weighting factor $W(\lambda)$ as shown in Equation (3).

$$Bxc(\lambda) = W(\lambda) \cdot Bx1(\lambda) + (1 - W(\lambda)) \cdot Bx2(\lambda) \qquad (3)$$

Similarly to Gaertner and Griesser's method, the above-mentioned weighting factor $W(\lambda)$ for each wavelength $\lambda$ is determined using a fluorescent standard containing a fluorescent substance with excitation-fluorescence characteristics, namely, the bi-spectral luminescent radiance factor $F(\mu,\lambda)$ substantially identical or similar to that of the sample to be measured and given a total spectral radiance factors $Bs(\lambda)$ under the specified test illumination. That is, the weighting factor $W(\lambda)$ is so determined for each wavelength $\lambda$ numerically that the synthesized total spectral radiance factor $Bxc(\lambda)$ by Equation (3) matches the given total spectral radiance factors $Bs(\lambda)$ under the specific test illumination. (see FIG. 1 of U.S. Pat. No. 5,636,015).

This method is equivalent to respectively performing the correction of the UV content in the illumination by Gaertner and Griesser's method for the total spectral radiance factor $Bx(\lambda)$ at each wavelength as the target instead of the single colorimetric value. Since the method gives the total spectral radiance factors $Bxc(\lambda)$ of the sample comparable to $Bs(\lambda)$ under the specific test illumination, the method has an advantage that all the colorimetric values derived therefrom are also comparable to those under the specific illumination. Although this method eliminates many shortcomings of Gaertner and Griesser's method such as the mechanical complicity, lack of reliability, and complicated and time-consuming operation, it still requires a fluorescent standard, and errors due to the difference between the spectral intensity of the illumination at the time of UV correction and that at the time of sample measurement thereafter still remains.

If paper is treated by FWA, colors printed thereon are affected by fluorescence of the paper i.e. a fluorescent substrate. Since the amount of excitation light reaching the paper depends on the spectral transmittance of ink covering the paper, the spectral excitation-fluorescence characteristics (spectral excitation efficiency and spectral fluorescence intensity) of the printed paper depend not only on the spectral excitation-fluorescence characteristics of the paper but also on an average spectral transmittance characteristic of a measuring area of paper including dot areas. The average spectral transmittance characteristic of the measuring area depends on a spectral transmittance characteristic of a whole printed surface printed with an ink at an area ratio of 100%, and a ratio of the dot area (relative area covered by ink) with respect to the measuring area of paper. Consequently, the spectral excitation-fluorescence characteristics of the measuring area depend on the spectral transmittance characteristic of the whole printed surface, and the ratio of the dot areas with respect to the measuring area. If paper is printed with two or more different inks, the paper is covered with the inks and the superposition of the inks, and accordingly, the spectral excitation-fluorescence characteristics of the measuring area depends on the spectral transmittances of the whole printed surfaces of the inks and the superposition of inks, and the area ratios of the dot areas. In other words, information on spectral transmittance characteristics of whole printed surfaces where inks are individually and superimposedly printed is required in order to measure an optical property of a printed surface on paper i.e. a fluorescent substrate where two or more different inks are printed, considering an effect of fluorescent light.

Ink with a transmittance characteristic having no dependence on the wavelength does not change the relative spectral intensity of the illumination light reaching the paper and equally influences to the spectral integrated excitation efficiency of the illumination synthesized by the method of U.S. Pat. No. 5,636,015 and to that of the test illumination. Accordingly, the synthesized total spectral radiance factor $Bxc(\lambda)$ of the printed surface is comparable to that to be obtained under the specified test illumination although it is different from that of an unprinted surface. Here, the spectral integrated excitation efficiency $E(\lambda)$ expressed by Equation (4) is the excitation efficiency for fluorescence at wavelength $\lambda$ excited by the whole illumination.

$$E(\lambda)=\int Q(\mu,\lambda)\cdot I(\mu)d\mu \qquad (4)$$

where $Q(\mu,\lambda)$ is the bi-spectral excitation efficiency, that is, the excitation efficiency for fluorescence at wavelength $\lambda$ excited by light of a unit intensity and of bandwidth $d\mu$ at wavelength $\mu$.

As described above, both simplified methods (Gaertner and Griesser's method and the method of U.S. Pat. No. 5,636, 015) need the fluorescent standard. Since the fluorescent standard made of the same material as the sample to be measured such as paper or fabric and containing the same fluorescent substance as that contained in the sample is unstable and requires considerable cares for controlling the change due to the aging and for the renewal. Further, errors due to the change of the spectral intensity of the illumination after the UV correction are inevitable, and as the result, frequent UV readjustments are required for avoiding these errors. In view of these, a method and an apparatus for measuring a fluorescent sample free from a fluorescent standard and a UV correction using the fluorescent standard are required. In order to accomplish the task, it is required to accurately acquire spectral transmittance characteristics of inks, in addition to an excitation-fluorescence characteristics of printed paper, and area ratios of the inks. However, the ink concentration differs among lots. Also, the thickness of each ink layer differs depending on a printing machine e.g. a printer, an ambient temperature, or a like factor. Accordingly, if a spectral transmittance characteristic different from a spectral transmittance characteristic of a whole printed surface printed with an ink at an area ratio of 100% under a specific printing condition such as a printing machine, an ink lot, an ambient temperature, or a like factor, in other words, a spectral transmittance characteristic of a whole printed surface in a different printing condition, despite the same ink area ratio of 100%, is used as a typical value, such an approach may cause a non-negligible measurement error.

SUMMARY OF THE INVENTION

In view of the above problems residing in the conventional examples, it is an object of the invention to provide an optical property measuring method and an optical property measuring apparatus that enable to obtain spectral transmittance characteristics of inks to be measured with sufficient precision in conformity with a printing condition of a printed sample to be measured, and accurately perform colorimetry of a printed color on a fluorescent substrate.

In an optical property measuring method and an optical property measuring apparatus according to an aspect of the invention, a spectral transmittance characteristic of a reference colored layer prepared as a reference is corrected based on a measured spectral reflection characteristic of a colored layer, and the spectral reflection characteristic of the reference colored layer. With this arrangement, information on the measured spectral transmittance characteristic of the colored layer can be obtained with sufficient precision in conformity with a printing condition of a sample to be measured. Thus, colorimetry of a printed color of a fluorescent sample i.e. a colored surface on a fluorescent substrate can be accurately performed by using the corrected spectral transmittance characteristic of the reference colored layer.

These and other objects, features and advantages of the present invention will become more apparent upon reading the following detailed description along with the accompanying drawings.

BRIEF DESCRIPTION OF THE DRAWINGS

FIGS. 2A and 2B are diagrams for describing how ink layers are formed one over the other, wherein FIG. 2A is a cross-sectional view schematically showing an arrangement that Y ink layer and M ink layer are formed one over the other on FWA treated paper, and FIG. 2B is a top plan view of FIG. 2A.

FIGS. 4A and 4B are a flowchart for measuring a total spectral radiance factor of a fluorescent sample by the optical property measuring apparatus.

DETAILED DESCRIPTION OF THE PREFERRED EMBODIMENTS

Figure 1:
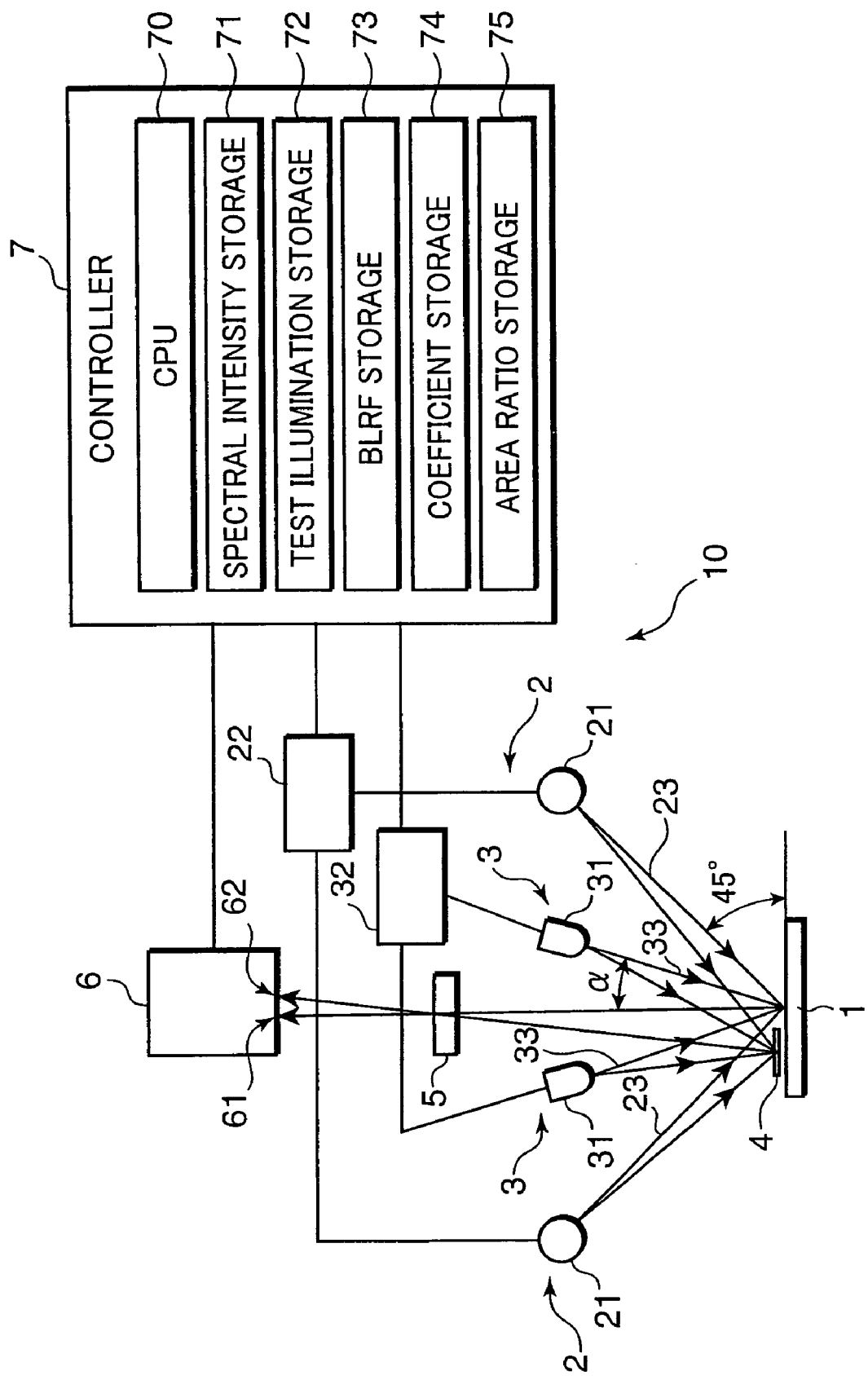
FIG. 1 is a schematic diagram showing an optical property measuring apparatus embodying the invention.

In the following, an embodiment of the invention is described referring to the drawings. The elements indicated by the same reference numerals throughout the drawings have the same construction, and repeated description thereof is omitted herein.

(Description on Optical Property Measuring Apparatus)

FIG. 1 is a schematic diagram showing an example of an apparatus for measuring an optical property of a fluorescent sample as an embodiment of the invention. As shown in FIG. 1, an optical property measuring apparatus 10 includes a sample 1 to be measured, a first illuminator 2, a second illuminator 3, a reference plane 4, a receiving optics 5, a dual channel spectral unit 6, and a controller 7. The sample 1 is a sample to be measured including fabrics, paper, or a like material containing a fluorescent substance. The sample 1 is disposed at a predetermined measurement position. The first illuminator 2 illuminates the sample 1. The first illuminator 2 has an incandescent lamp 21 as a light source, and a first driver 22 for driving the incandescent lamp 21 to turn on the incandescent lamp 21 e.g. in a pulse-like manner. Similarly to the first illuminator 2, the second illuminator 3 illuminates the sample 1. The second illuminator 3 has ultraviolet LEDs 31, as an ultraviolet light source, for outputting a light flux in an ultraviolet region, and a second driver 32 for driving the ultraviolet LEDs 31 to turn on the ultraviolet LEDs 31 e.g. in a pulse-like manner. The light source of the second illuminator 3 is not limited to the ultraviolet LEDs 31. As far as a light source is capable of outputting a light flux in an ultraviolet region, any light source including a xenon flash lamp may be used.

The reference plane 4 is a white and diffusively reflecting plane as a reference surface or a reflecting surface. The reference plane 4 is disposed near a measuring area of the sample 1. The receiving optics 5 as a light receiving system has an optical lens or lenses. The receiving optics 5 receives a light component in a normal direction of light emitted from the sample 1 illuminated by the first illuminator 2 and the second illuminator 3, and a light component in a normal direction of reflecting light from the reference plane 4, and causes the received light flux to be incident toward the dual channel spectral unit 6 to be described later.

The dual channel spectral unit 6 performs spectral measurement of light incident from the receiving optics 5. The dual channel spectral unit 6 has a first incident slit 61 and a second incident slit 62. Light emitted from the sample 1 illuminated with a below-mentioned light flux LA or light flux LB is incident onto the first incident slit 61. On the other hand, reflecting light from the reference plane 4 illuminated with the light flux LA or the light flux LB is incident onto the second incident slit 62. The dual channel spectral unit 6 performs spectral measurement of sample light incident onto the first incident slit 61 to output spectral intensity data on the sample light, as a first channel output, and performs spectral measurement of reference light incident onto the second incident slit 62, in other words, the light flux LA or the light flux LB to output spectral intensity data on the light flux LA or the light flux LB as a second channel output. The dual channel spectral unit 6 is an example of a spectral measuring unit, and functions as the spectral measuring unit.

The controller 7 includes an ROM (Read Only Memory) for storing control programs or the like, an RAM (Random Access Memory) for storing data on computation processing or control processing, and a CPU (Central Processing Unit) for reading the control program or the like from the ROM for execution. The controller 7 controls overall operations of the optical property measuring apparatus 10. Specifically, the controller 7 controls driving on emission operations of the first illuminator 2 and the second illuminator 3, and light receiving and spectral operations of the dual channel spectral unit 6. The controller 7 also executes various computation processing on calculation of a total spectral radiance factor or calibration of a relative spectral sensitivity with respect to the sample 1, based on spectral information from the dual channel spectral unit 6. The various computing functions of the controller 7 will be described later.

In use of the optical property measuring apparatus 10 having the above components, when the controller 7 drives the first driver 22 to turn on the incandescent lamp 21, the incandescent lamp 21 illuminates the sample 1 with a light flux 23 at an incident angle of about 45° with respect to the normal to the sample 1. Similarly, when the controller 7 drives the second driver 32 to turn on the ultraviolet LEDs 31, the ultraviolet LED 31 illuminates the sample 1 with a light flux 33 in a direction close to the normal than the incident angle 45° of the light flux 23 i.e. at an incident angle indicated by the symbol "α".

In this embodiment, the first illuminator 2 is also called as an illuminant A, and the first illuminator 2 and the second illuminator 3 are generically called as an illuminant B. The light flux LA outputted from the illuminant A having the incandescent lamp 21 as the only one light source, hardly has a light intensity in an excitation region i.e. an ultraviolet region. On the other hand, the light flux LB outputted from the illuminant B having the incandescent lamp 21 and the ultraviolet LEDs 31 as light sources, in other words, the light flux LB outputted from the illuminant B in the case where the incandescent lamp 21 and the ultraviolet LEDs 31 are simultaneously turned on, has a sufficient light intensity in the excitation region. Both of the illuminants A and B have an intensity in the visible region that enables to calculate an excitation intensity with respect to an intensity of each wavelength, and accordingly enables to calculate a fluorescent spectral radiance factor or a total spectral radiance factor. In performing measurement by using illumination light having no spectral intensity in the visible region, the aforementioned calculation cannot be performed, and a fluorescent spectral radiance factor or a total spectral radiance factor cannot be calculated.

The near-normal component of the light emitted from the sample 1 illuminated with the light flux LA or the light flux LB is incident from the receiving optics 5 onto the first incident slit 61 of the dual channel spectral unit 6 and spectrally measured by the dual channel spectral unit 6. Then, a spectral intensity $Sx1(\lambda)$ or $Sx2(\lambda)$ of the incident light component is outputted to the controller 7 as the first channel output. On the other hand, the reference plane 4 disposed near the measuring area of the sample 1 is illuminated with the light flux LA or the light flux LB simultaneously with the surface of the sample 1. Then, the near-normal component of the reflecting light from the reference plane 4 is incident from the receiving optics 5 onto the second incident slit 62 of the dual channel spectral unit 6, and spectrally measured by the dual channel spectral unit 6. Then, a spectral intensity $Mx1(\lambda)$ or $Mx2(\lambda)$ of the incident light component is outputted to the controller 7 as the second channel output.

Figure 9:
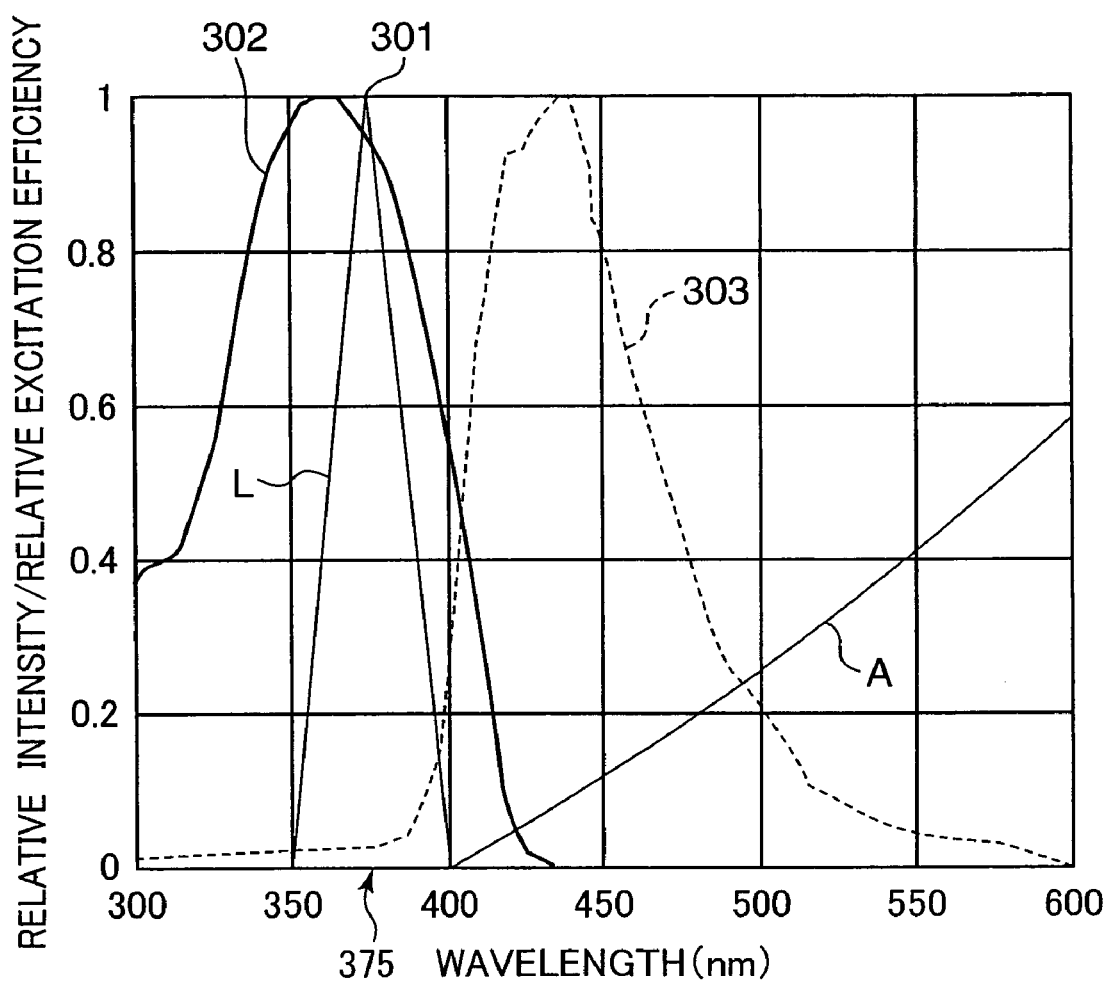
FIG. 9 is a graph showing spectral intensities of an incandescent lamp and an ultraviolet LED.
Figure 10:
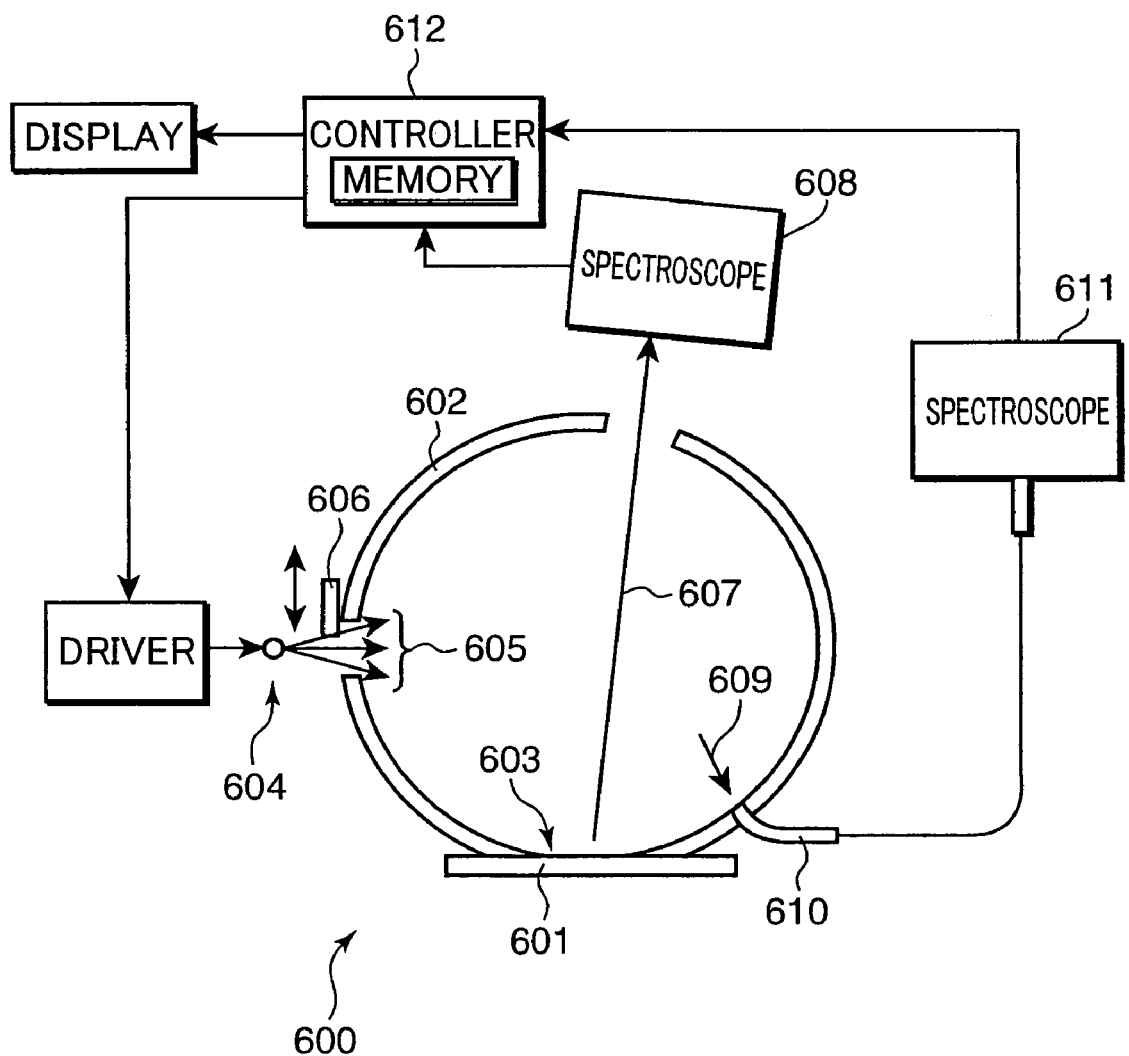
FIG. 10 is a schematic diagram showing a conventional measuring apparatus.
Figure 11:
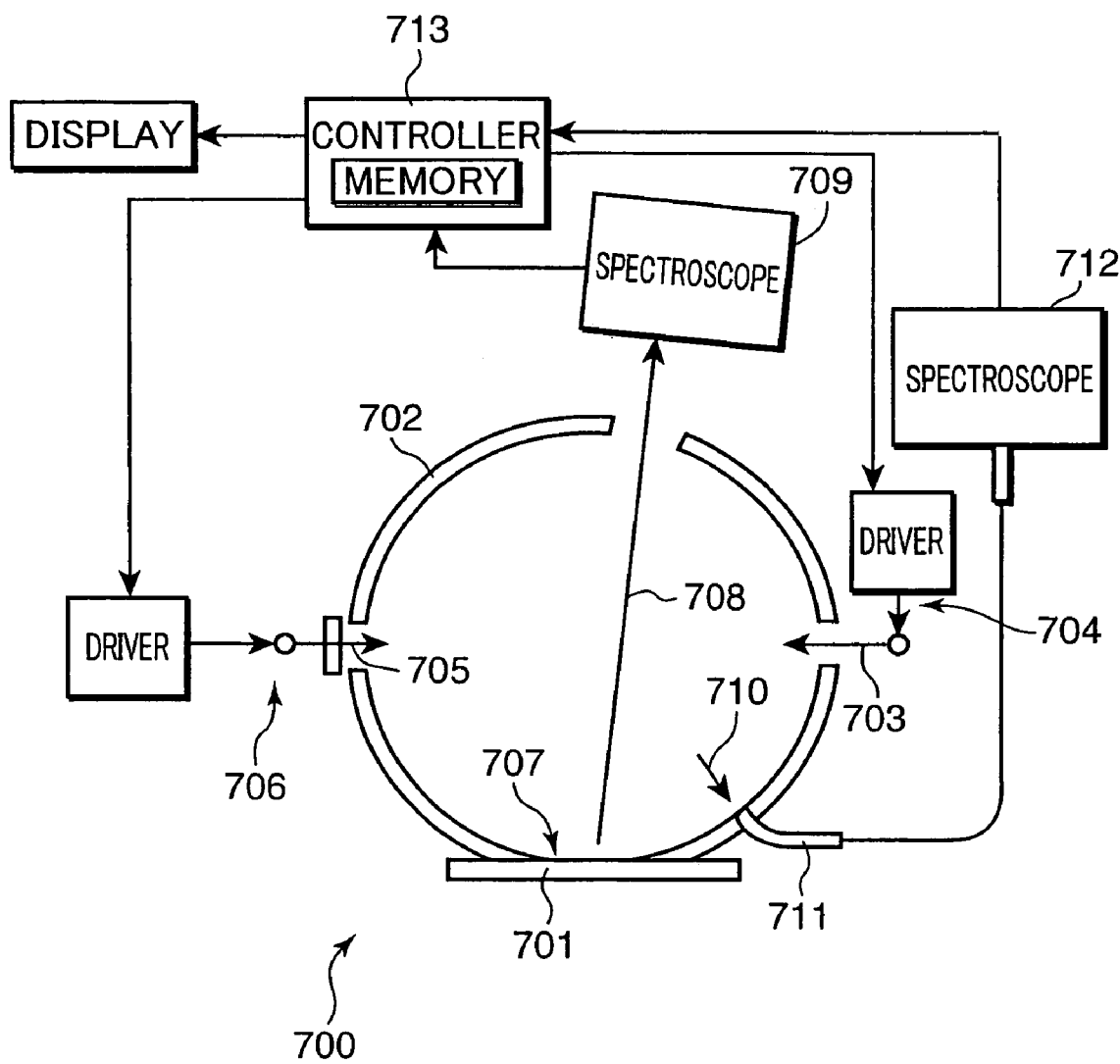
FIG. 11 is a schematic diagram showing another conventional measuring apparatus.

The center wavelength of the ultraviolet LEDs 31 in the second illuminator 3 is about 375 nm. As shown in the graph of FIG. 9 showing spectral intensities of a typical incandescent lamp and a typical ultraviolet LED, wherein the symbol A indicates a spectral intensity of the incandescent lamp, and the symbol L indicates a spectral intensity of the ultraviolet LED, a center wavelength 301 of the ultraviolet LED 31 is located near the peak of a spectral excitation efficiency 302 i.e. a relative spectral excitation efficiency of a typical FWA. The spectral excitation efficiency is an excitation efficiency of excitation light for exciting fluorescent light of the wavelength λ at each wavelength. An intensity i.e. an integrated excitation of fluorescent light of the wavelength λ to be excited by the illumination light is obtained by convolution integral with the spectral intensity of illumination light. The linear expression indicated by the reference numeral 303 shows a fluorescent spectral intensity i.e. a relative fluorescent spectral intensity of the FWA.

The technology disclosed in the embodiment requires to know a spectral intensity of illumination light. In view of this, the dual channel spectral unit 6 covers a wavelength range from about 360 nm to 740 nm including a wavelength range of light emitted from the ultraviolet LEDs 31. In other words, spectroscopic measurement in the wavelength range from about 360 nm to 740 nm is allowed. The illuminant B having the incandescent lamp 21 and the ultraviolet LEDs 31 as light sources emits light for a predetermined period that does not cause triplet effect. The triplet effect may occur if a fluorescent substance is illuminated with strong and short pulse light, and may harm compatibility with visual observation. Briefly explaining, the triplet effect is an excitation phenomenon i.e. a light absorption phenomenon accompanied by transition of electron state of molecule between singlet and triplet i.e. S and T levels, resulting from illumination light with a short emission period and a high excitation energy. In a normal condition, the probability of transition between S and T levels is extremely low.

The optical system of the optical property measuring apparatus 10 has 45/0 geometry (geometry for measuring a reflection characteristic: 45 degrees/0 degree) by combined arrangement of the first illuminator 2 and the receiving optics 5 as described above. The aforementioned geometry is used to control specular reflection from the sample 1. Specular reflection by the second illuminator 3 having no spectral intensity in the visible region does not affect colorimetry. Accordingly, the second illuminator 3 can be arranged at any position without constraints of the geometry.

In the following, details of the functional parts of the controller 7 are described. As shown in FIG. 1, the controller 7 includes a CPU 70, a spectral intensity storage 71, a test illumination storage 72, a BLRF (bi-spectral luminescent radiance factor) storage 73, a coefficient storage 74, and an area ratio storage 75. The CPU 70 is a circuit for performing various computation processing such as computation on driving control of the first illuminator 2, the second illuminator 3, and the dual channel spectral unit 6, and computation on calculation of a total spectral radiance factor or calibration of a relative spectral sensitivity with respect to the sample 1. The spectral intensity storage 71 is a circuit for storing spectral intensity data on emission light and illumination light that have been measured by the dual channel spectral unit 6 and sent from the dual channel spectral unit 6. The test illumination storage 72 is a circuit for storing predetermined spectral intensity data on reference illumination light. The BLRF storage 73 is a circuit for storing predetermined data on bi-spectral luminescent radiance factor approximate to that of the sample 1 i.e. a fluorescent sample.

The coefficient storage 74 is a circuit for storing coefficient data such as a sensitivity calibration coefficient to be used in calibrating a relative spectral sensitivity of the dual channel spectral unit 6; a conversion coefficient to be used in converting a spectral intensity of reflecting light (hereinafter, called as "reference light") from the reference plane 4 into a spectral intensity of illumination light (hereinafter, called as "sample illumination") for illuminating the sample 1; and a calibration coefficient to be used in obtaining a total spectral radiance factor of the sample 1, based on spectral intensities of light (hereinafter, called as "sample light") emitted from the sample 1, and the reference light. The area ratio storage 75 is a circuit for storing area ratio data on the area ratios of printed areas where individual inks and combination of the inks are printed, which is used in colorimetry of a printed surface to be described later.

The controller 7 performs measurement control i.e. computation on the following factors (A) and (B), based on the spectral intensity data on emission light and illumination light, the spectral intensity data on test illumination, the data on the bi-spectral luminescent radiance factor, and the data on the sensitivity calibration coefficient, the conversion coefficient, and the calibration coefficient.

(A) A total spectral radiance factor to be obtained in the case where the sample is illuminated with test illumination

[Principle of Measurement]

Generally, use of the aforementioned bi-spectro-fluorometer or a measuring apparatus with an illuminator for projecting illumination light having substantially the same spectral intensity as test illumination I s is required to obtain a spectral radiance factor of a fluorescent sample when the fluorescent sample is illuminated with the test illumination I s. On the other hand, the embodiment provides a technique of numerically synthesizing virtual illumination capable of giving a fluorescent spectral radiance factor substantially identical to a fluorescent spectral radiance factor of specific test illumination with respect to a fluorescent sample having excitation-fluorescence characteristics approximate to a specific bi-spectral luminescent radiance factor. Specifically, assuming that a bi-spectral luminescent radiance factor of the fluorescent sample is $F(\mu,\lambda)$, a spectral intensity of the test illumination I s is I s($\lambda$), and a spectral intensity of the numerically synthesized illumination light (hereinafter, called as "synthesized illumination") I c is I c($\lambda$), a fluorescent spectral radiance factor $F(\lambda)(=\int F(\mu,\lambda)\cdot I(\mu)d\mu/I(\lambda))$ by the respective illuminations is obtained by synthesized illumination I c satisfying the following Equation (5). The synthesized illumination I c is obtained by a spectral intensity i.e. synthesis obtained by linear combination of illuminations I 1 and I 2 whose relative intensities in the excitation region and the fluorescent region are different from each other. The spectral intensity I($\lambda$) is equivalent to that of reflecting light from a surface of a perfect diffuse reflector, with a suitable proportional constant, as described above.

$$\int F(\mu,\lambda)\cdot Is(\mu)d\mu/Is(\lambda) = \int F(\lambda,\lambda)\cdot Ic(\mu)d\mu/Ic(\lambda) \quad (5)$$

In the synthesis by the weighted linear combination of the illuminations I 1 and I 2, assuming that weighting factors of linear combination to be set at each wavelength are W($\lambda$) and (1−W($\lambda$)), the spectral intensity I c($\lambda$) of the synthesized illumination I c is expressed by the following Equation (6) by using the spectral intensities I 1($\lambda$) and I 2($\lambda$) of the illuminations I 1 and I 2.

$$Ic(\lambda) = W(\lambda)\cdot I1(\lambda) + (1-W(\lambda))\cdot I2(\lambda) \quad (6)$$

Thereby, the fluorescent spectral radiance factor Fc($\lambda$) by the synthesized illumination I c is expressed by the following Equation (7).

$$Fc(\lambda) = \int F(\mu,\lambda)\cdot Ic(\mu)d\mu/Ic(\lambda) = \int F(\mu,\lambda)\cdot[W(\lambda)\cdot I1(\mu)+(1-W(\lambda))\cdot I2(\mu)]d\mu/[W(\lambda)\cdot I1(\lambda)+(1-W(\lambda))\cdot I2(\lambda)] \quad (7)$$

Accordingly, the above Equation (5) is rewritten into the following Equation (8).

$$\int F(\mu,\lambda)\cdot Is(\mu)d\mu/Is(\lambda) = \int F(\mu,\lambda)\cdot[W(\lambda)\cdot I1(\mu)+(1-W(\lambda))\cdot I2(\mu)]d\mu/[W(\lambda)\cdot I1(\lambda)+(1-W(\lambda))\cdot I2(\lambda)] \quad (8)$$

Then, the weighting factor W($\lambda$) is calculated based on the Equation (8). Specifically, the bi-spectral luminescent radiance factor $F(\mu,\lambda)$ in the Equation (8) and the spectral intensity I s(λ)=I s(μ) of test illumination Is are given as predetermined numerical data and stored. The spectral intensities I 1 (λ) and I 2(λ) of actual illuminations I 1 and I 2 are measured by actual measurement. Specifically, I 1(λ) and I 2(λ) are obtained by performing conversion with respect to the spectral intensity of actually measured reference light. Thus, the weighting factor W(λ) is calculated by computation alone. Then, calculated is a total spectral radiance factor Bxs(λ) in the case where the fluorescent sample having a bi-spectral luminescent radiance factor approximate to the bi-spectral luminescent radiance factor F(μ, μ) used in the calculation is illuminated with the same test illumination I s. In other words, the total spectral radiance factor Bs(λ) is obtained by the following Equation (11), based on a calibration constant C(λ), and Sxc(λ) and I c(λ). Sxc(λ) and I c(λ) are given by the following Equations (9) and (10), which express that spectral intensities Sx1(λ) and Sx2(λ) of sample light in the case where the fluorescent sample is illuminated with the illuminations I 1 and I 2, and spectral intensities I 1(λ) and I 2(λ) of the illuminations I 1 and I 2 are synthesized by linear combination with use of the weighting factors W(λ) and (1−W(λ)), respectively.

$$Sxc(\lambda)=W(\lambda)\cdot Sx1(\lambda)+(1-W(\lambda))\cdot Sx2(\lambda) \quad (9)$$

$$Ic(\lambda)=W(\lambda)\cdot I1(\lambda)+(1-W(\lambda))\cdot I2(\lambda) \quad (10)$$

where Sxc(λ) is a spectral intensity of light emitted from the sample in the case where the sample is illuminated with the synthesized illumination I c, and I c(λ) is a spectral intensity of the synthesized illumination I c to be synthesized by weighted linear combination of the illuminations I 1 and I 2.

$$Bs(\lambda)=C(\lambda)\cdot Sc(\lambda)/Ic(\lambda) \quad (11)$$

The aforementioned computation can be simplified by using the illuminations I 1 and I 2 each having an intensity in the visible region, as described in the embodiment, for instance, by using the light flux LA as the illumination I 1, and the light flux LB as the illumination I 2. Specifically, illuminations I 1(F)/I 1(λ) and I 2(μ)/I 2(λ) obtained by calculating the illuminations I 1 and I 2 with respect to the intensity at the wavelength λ in the visible region are estimated, and I 1λ(I) and I 2λ (μ) are computed, wherein I 1λ (μ)=I 1(μ)/I 1(λ), and I 2λ (μ)=I 2(μ)/I 2(λ). Therefore, I 1λ(μ)=I 2λ(λ)=1. By this processing, light sources which are different from each other at each wavelength λ in the visible region are estimated. In this computation, the denominator in the right side of the Equation (8) is [W(λ) I 1λ(λ)+(1−W(λ))·I 2λ(λ)], and the value thereof is constantly "1". Therefore, the Equation (7) is rewritten into the following Equation (12). The fluorescent spectral radiance factor Fc(λ) by the synthesized illumination I c is expressed by linear combination of the fluorescent spectral radiance factors with the illuminations I 1 and I 2.

$$\int F(\mu,\lambda)\cdot Ic(\mu)d\mu/Ic(\lambda)=W(\lambda)\cdot\int F(\mu,\lambda)\cdot I1\lambda(\mu)d\mu+(1-W(\lambda))\cdot\int F(\mu,\lambda)\cdot I2\lambda(\mu)d\mu=W(\lambda)\cdot\int F(\mu,\lambda)\cdot I1(\mu)d\mu/I1(\lambda)+(1-W(\lambda))\cdot\int F(\mu,\lambda)\cdot I2(\mu)d\mu/I2(\lambda) \quad (12)$$

Thereby, the Equation (5) is rewritten into the following Equation (13).

$$\int F(\mu,\lambda)\cdot Is(\mu)d\mu/Is(\lambda)=W(\lambda)\cdot\int F(\mu,\lambda)\cdot I1(\mu)d\mu/I1(\lambda)+(1-W(\lambda))\cdot\int F(\mu,\lambda)\cdot I2(\mu)d\mu/I2(\lambda) \quad (13)$$

The Equation (12) expresses that the fluorescent spectral radiance factor Fc(λ) can be obtained by the synthesized illumination I c(μ), which is expressed by the following Equation (12') and which is different at each wavelength λ in the visible region. I c(μ) is a weighted summation of two virtual illuminations whose intensity at the wavelength λ is "1" and which are different from each other at each wavelength λ, i.e. I 1λ(μ)=I 1(μ)/I 1(λ) and I 2λ(μ)=I 2(μ)/I 2(λ), with use of the weighting factors W(λ) and (1−W(λ)).

$$Ic(\mu)=W(\lambda)\cdot I1(\mu)/I1(\lambda)+(1-W(\lambda))\cdot I2(\mu)/I2(\lambda) \quad (12')$$

Similarly to the computation of obtaining the weighting factor W(λ) based on the Equation (8), the weighting factor W(λ) can be obtained by merely solving the Equation (13), if the bi-spectral luminescent radiance factor F(μ,λ) of the fluorescent sample, the spectral intensity I s(λ) of the test illumination I s, and the spectral intensities I 1(λ) and I 2(λ) of the two illuminations I 1 and I 2 are given.

In the conventional method recited in U.S. Pat. No. 5,636, 015, the spectral intensities I 1(λ) and I 2(λ) of actual illuminations I 1 and I 2 are unknown. Accordingly, it can be interpreted that the integral in the right side of the Equation (13) is replaced by an actually measured value of a total spectral radiance factor of a fluorescent standard.

Thus, the weighting factor W(λ) derived from the Equation (13) is used for the fluorescent sample having the bi-spectral luminescent radiance factor approximate to the bi-spectral luminance radiance factor F(μ,λ) used in the calculation, and a fluorescent spectral radiance factor Fxc(λ) of the fluorescent sample by the synthesized illumination I c can be expressed by linear combination of the fluorescent spectral radiance factors Fx1(λ) and Fx2(λ) of the sample by the illuminations I 1 and I 2 i.e. the light fluxes LA and LB (see the Equation (14)).

$$Fxc(\lambda)=W(\lambda)\cdot Fx1(\lambda)+(1-W(\lambda))\cdot Fx2(\lambda) \quad (14)$$

Also, the total spectral radiance factor Bxc(λ), which is the sum of the fluorescent spectral radiance factor Fxc(λ), and a reflection spectral radiance factor Rxc(λ) which does not depend on illumination light, can be obtained by linear combination of total spectral radiance factors Bx1(λ) and Bx2 (λ) obtained by actual measurement of the fluorescent sample illuminated with the illuminations I 1 and I 2, by using the same weighting factor W(λ) (see the Equation (15).

$$Bxc(\lambda)=W(\lambda)\cdot Bx1(\lambda)+(1-W(\lambda))\cdot Bx2(\lambda) \quad (15)$$

In the above description, the weighting factor W(λ) is obtained by deriving the bi-spectral luminescent radiance factor F(μ,λ) and using the Equation (8) or (13). Alternatively, the weighting factor W(λ) may be obtained in the similar manner as mentioned above, by substituting the bi-spectral radiance factor B(μ,λ) for F(μ,λ) in the Equation (8) or (13), because Bc(λ)=Bs(λ) if Fc(λ)=Fs(λ) from the Equation (1).

Two kinds of calibrations are necessary prior to measuring an optical property of the fluorescent sample. In the following, the two kinds of calibrations are described.

1. Calibration of the Relative Spectral Sensitivity of the Spectral Unit

As described above, the method of the embodiment requires to know a spectral intensity of actual illumination in the measuring apparatus. In view of this, a relative spectral sensitivity of a spectral measuring unit (in this embodiment, the dual channel spectral unit 6) is calibrated at the time of manufacturing. First, wavelength calibration is performed for the spectral measuring unit by a well-known method. Then, a sensitivity calibration coefficient G(λ) is obtained based on an output Sa(λ), which is obtained by outputting a light flux from a light source such as A illuminant having a known spectral intensity distribution A(λ).

$$G(\lambda)=A(\lambda)/Sa(\lambda) \quad (16)$$

2. White Calibration

In white calibration to be performed prior to measurement, the following two kinds of coefficients <1> and <2> are obtained based on spectral intensities $Sw1(\lambda)$ and $Sw2(\lambda)$ of sample light i.e. light emitted from a white calibration standard, and based on spectral intensities $Mw1(\lambda)$ and $Mw2(\lambda)$ of reference light i.e. reflecting light from the reference plane 4 to be obtained in the case where the white calibration standard having a known reflection spectral radiance factor $Rw(\lambda)$ and having no fluorescent characteristic, is illuminated with the illuminations I 1 and I 2 i.e. the light fluxes LA and LB.

<1> Conversion coefficients $D1(\lambda)$ and $D2(\lambda)$ for converting the spectral intensities $Mx1(\lambda)$ and $Mx2(\lambda)$ of reference light into the spectral intensities $I1(x)$ and $I2(\lambda)$ of sample illumination In this computation, conversion coefficients $D1(\lambda)$ and $D2(\lambda)$ for converting the spectral intensities $Mx1(\lambda)$ and $Mx2(\lambda)$ of reference light at the time of sample measurement into the spectral intensities $I1(\lambda)$ and $I2(\lambda)$ of sample illumination are obtained by the following Equations (17) and (18), based on the spectral intensities $Sw1(\lambda)$ and $Sw2(\lambda)$ of sample light and the spectral intensities $Mw1(\lambda)$ and $Mw2(\lambda)$ of reference light to be obtained in the case where the white calibration standard having the known reflection spectral radiance factor $Rw(\lambda)$ is illuminated with illuminations I 1 and I 2, and based on the sensitivity calibration coefficient $G(\lambda)$ expressed by the Equation (16).

$$D1(\lambda) = [G(\lambda) \cdot Sw1(\lambda)] / [Mw1(\lambda) \cdot Rw(\lambda)] \quad (17)$$

$$D2(\lambda) = [G(\lambda) \cdot Sw2(\lambda)] / [Mw2(\lambda) \cdot Rw(\lambda)] \quad (18)$$

By the above computation, assuming that the spectral intensities of reference light at the time of measuring the fluorescent sample are $Mx1(\lambda)$ and $Mx2(\lambda)$, spectral intensities $I1(\lambda)$ and $I2(\lambda)$ of sample illumination can be obtained by the following Equations (19) and (20) by using the conversion coefficients $D1(\lambda)$ and $D2(\lambda)$, respectively.

$$I1(\lambda) = D1(\lambda) \cdot Mx1(\lambda) \quad (19)$$

$$I2(\lambda) = D2(\lambda) \cdot Mx2(\lambda) \quad (20)$$

<2> Calibration coefficients $C1(\lambda)$ and $C2(\lambda)$ for deriving the total spectral radiance factors $Bx1(\lambda)$ and $Bx2(\lambda)$ of the fluorescent sample based on the spectral intensities $Sx1(\lambda)$ and $Sx2(\lambda)$ of sample light, and the spectral intensities $Mx1(\lambda)$ and $Mx2(\lambda)$ of reference light to be obtained when the sample is illuminated with illuminations I 1 and I 2

In this computation, calibration coefficients $C1(\lambda)$ and $C2(\lambda)$ are obtained by the following Equations (21) and (22), based on the known reflection spectral radiance factor $Rw(\lambda)$, the spectral intensities $Sw1(\lambda)$ and $Sw2(\lambda)$ of sample light, and the spectral intensities $Mw1(\lambda)$ and $Mw2(\lambda)$ of reference light to be obtained when the white calibration standard is illuminated with the illuminations I 1 and I 2, as described in (1).

$$C1(\lambda) = Rw(\lambda) / [Sw1(\lambda) / Mw1(\lambda)] \quad (21)$$

$$C2(\lambda) = Rw(\lambda) / [Sw2(\lambda) / Mw2(\lambda)] \quad (22)$$

By the above computation, assuming that the spectral intensities of sample light and reference light to be obtained when the fluorescent sample is illuminated with the illuminations I 1 and I 2 at the time of measuring the fluorescent sample are $Sx1(\lambda)$, $Sx2(\lambda)$, $Mx1(\lambda)$, and $Mx2(\lambda)$, the total spectral radiance factors $Bx1(\lambda)$ and $Bx2(\lambda)$ of the sample surface can be obtained by the following Equations (23) and (24).

$$Bx1(\lambda) = C1(\lambda) \cdot Sx1(\lambda) / Mx1(\lambda) \quad (23)$$

$$Bx2(\lambda) = C2(\lambda) \cdot Sx2(\lambda) / Mx2(\lambda) \quad (24)$$

The aforementioned measurement principle on the total spectral radiance factor in the case where the fluorescent sample is illuminated with the test illumination can also be summarized as follows.

a1. A spectral characteristic of fluorescent light emitted from the fluorescent sample illuminated with arbitrary illumination light is obtained based on a spectral intensity of illumination light, and a bi-spectral luminescent radiance factor of the sample (see the Equation (2)).

a2. Accordingly, if the spectral intensity of the illumination light is known, a total spectral radiance factor of a virtual fluorescent standard having a known bi-spectral luminescent radiance factor can be calculated, and the virtual fluorescent standard can be replaced by an actual fluorescent standard.

a3. The approach described in D1 is applied to the virtual fluorescent standard.

a4. The spectral intensity of test illumination is given as data in advance, and the spectral intensity of actual illumination light in the measuring apparatus is obtained by actual measurement.

<Procedure for Measuring the Total Spectral Radiance Factor of a Fluorescent Sample>

Figure 3:
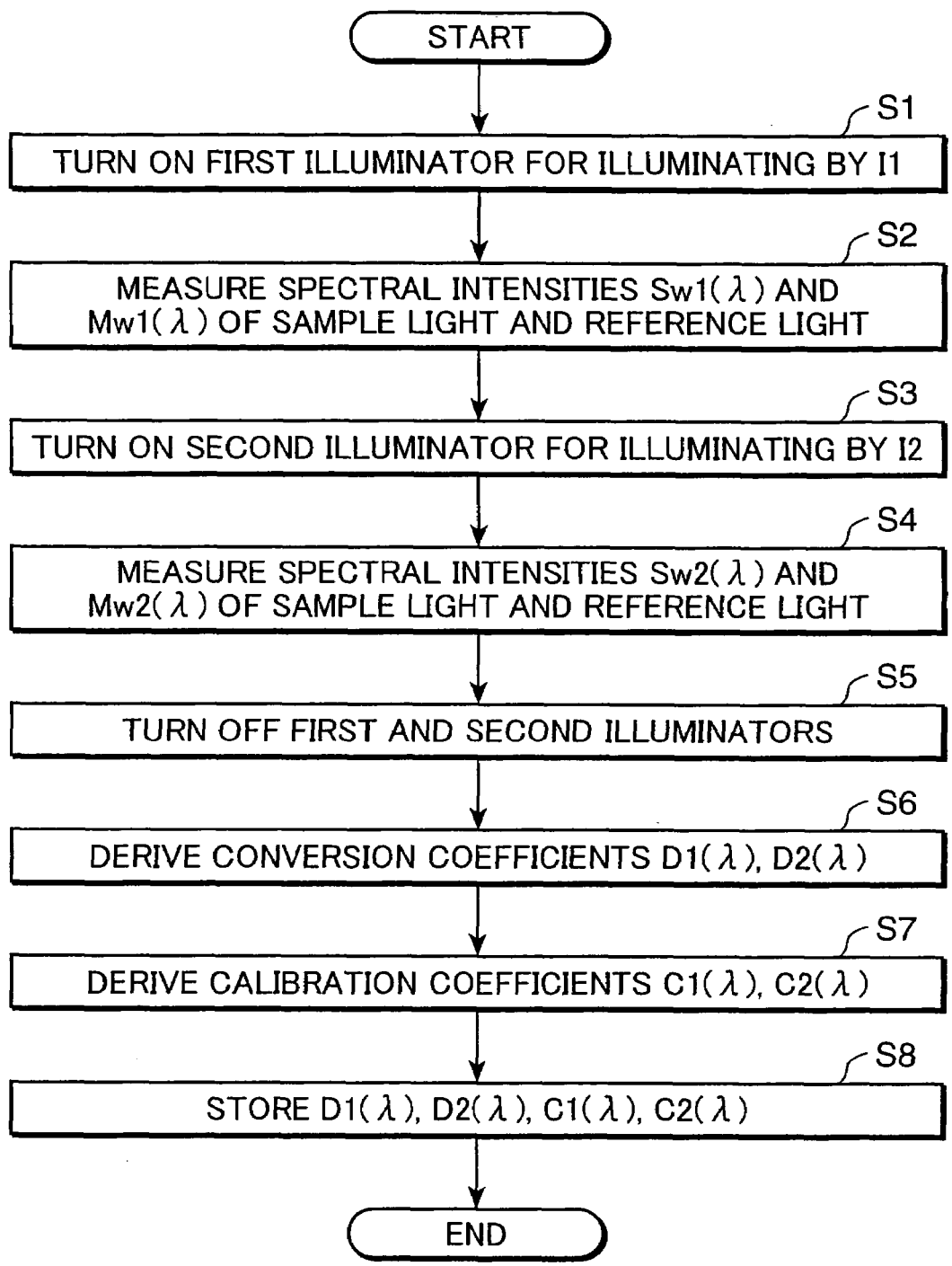
FIG. 3 is a flowchart on white calibration to be performed by an optical property measuring method embodying the invention.

A total spectral radiance factor of a fluorescent sample is measured by the optical property measuring apparatus 10 in accordance with a flowchart shown in FIGS. 4A and 4B, after the white calibration is performed by a flowchart shown in FIG. 3. FIG. 3 is a flowchart showing an example of the white calibration. First, the controller 7 turns on the incandescent lamp 21 of the first illuminator 2 to illuminate a sample for white calibration disposed in the measurement aperture i.e. a white calibration standard having a known reflection spectral radiance factor $Rw(\lambda)$ and having no fluorescent characteristic, with the light flux LA i.e. the illumination I 1 (Step S1). Then, the controller 7 causes the dual channel spectral unit 6 as the spectral measuring unit to measure the spectral intensity $Sw1(\lambda)$ of sample light by the light flux LA, and the spectral intensity $Mw1(\lambda)$ of reference light by the illumination LA, and stores the spectral intensity information on $Sw1(\lambda)$ and $Mw1(\lambda)$ into the spectral intensity storage 71 (Step S2). In this example, sample reflecting light is obtained from the white calibration standard as the sample light, because the white calibration standard has no fluorescent characteristic.

Then, the controller 7 turns on the ultraviolet LEDs 31 of the second illuminator 3 in a state that the on-state of the first illuminator 2 in Step S1 is maintained so that the sample 1 is illuminated with the light flux LB i.e. the illumination I 2 by the first illuminator 2 and the second illuminator 3 (Step S3). Then, similarly to Step S2, the controller 7 causes the dual channel spectral unit 6 to measure the spectral intensity $Sw2(\lambda)$ of sample light by the light flux LB and the spectral intensity $Mw2(\lambda)$ of reference light by the light flux LB, and stores the spectral intensity information on $Sw2(\lambda)$ and $Mw2(\lambda)$ into the spectral intensity storage 71 (Step S4). Then, the controller 7 turns off the first illuminator 2 and the second illuminator 3 (Step S5).

Then, the controller 7 calculates the conversion coefficients $D1(\lambda)$ and $D2(\lambda)$ for converting the spectral intensities $Mx1(\lambda)$ and $Mx2(\lambda)$ of reference light at the time of sample measurement into the spectral intensities $I1(\lambda)$ and $I2(\lambda)$ of sample illumination by the Equations (17) and (18), based on the spectral intensities $Sw1(\lambda)$ and $Sw2(\lambda)$ of sample light and the spectral intensities $Mw1(\lambda)$ and $Mw2(\lambda)$ of reference light obtained in Steps S3 and S4, and based on the sensitivity calibration coefficient $G(\lambda)$ expressed by the Equation (16) (Step S6).

Then, the controller 7 calculates the calibration coefficients $C1(\lambda)$ and $C2(\lambda)$ by the Equations (21) and (22), based on the spectral intensities $Sw1(\lambda)$ and $Sw2(\lambda)$ of sample light and the spectral intensities $Mw1(\lambda)$ and $Mw2(\lambda)$ of reference light obtained in Steps S2 and S4, and based on the known reflection spectral radiance factor $Rw(\lambda)$ (Step S7). Then, the controller 7 stores the data on the conversion coefficients $D1(\lambda)$ and $D2(\lambda)$ calculated in Step S6, and the calibration coefficients $C1(\lambda)$ and $C2(\lambda)$ calculated in Step S7 into a predetermined storage e.g. the coefficient storage 74 (Step S8).

FIGS. 4A and 4B are a flowchart showing an example of measuring a total spectral radiance factor of a fluorescent sample by the optical property measuring apparatus 10. First, the test illumination I s is selected prior to measurement. Specifically, the controller 7 reads, from the test illumination storage 72, the spectral intensity data I s$(\lambda)$ i.e. the spectral intensity I s$(\lambda)$ of the test illumination I s to be selected (Step S11). Then, the controller 7 selects the type of the sample 1. Specifically, the controller 7 reads, from the BLRF storage 73, the data on the bi-spectral luminescent radiance factor $F(\mu,\lambda)$ approximate to that of the sample 1 (Step S12). Then, the controller 7 turns on the incandescent lamp 21 of the first illuminator 2 to illuminate the sample 1 disposed in the measurement aperture with the light flux LA i.e. the illumination I 1 (Step S13). Then, the controller 7 causes the dual channel spectral unit 6 as the spectral measuring unit to measure the spectral intensity $Sx1(\lambda)$ of sample light by the light flux LA and the spectral intensity $Mx1(\lambda)$ of reference light by the light flux LA, and stores the spectral intensity information on $Sx1(\lambda)$ and $Mx1(\lambda)$ into the spectral intensity storage 71 (Step S14).

Then, the controller 7 turns on the ultraviolet LEDs 31 of the second illuminator 3 in a state that the on-state of the first illuminator 2 in Step S13 is maintained so that the sample 1 is illuminated with the light flux LB i.e. the illumination I 2 by the first illuminator 2 and the second illuminator 3 (Step S15). Then, similarly to Step S14, the controller 7 causes the dual channel spectral unit 6 to measure the spectral intensity Sx2 $(\lambda)$ of sample light by the light flux LB and the spectral intensity $Mx2(\lambda)$ of reference light by the light flux LB, and stores the spectral intensity information on $Sx2(\lambda)$ and $Mx2(\lambda)$ into the spectral intensity storage 71 (Step S16). Then, the controller 7 turns off the first illuminator 2 and the second illuminator 3 (Step S17).

Then, the controller 7 calculates the fluorescent spectral radiance factor $Fs(\lambda)$ by test illumination by the following Equation (25), based on the spectral intensity data I s$(\lambda)$=I s(s) and the bi-spectral luminescent radiance factor $F(\mu,\lambda)$, which have been read out in Steps S11 and S12, respectively (Step S18).

$$Fs(\lambda) = \int F(\mu,\lambda) \cdot Is(\mu) d\mu / Is(\lambda) \quad (25)$$

Then, the controller 7 converts the spectral intensities $Mx1(\lambda)$ and $Mx2(\lambda)$ of reference light by the light fluxes LA and LB into the spectral intensities I $1(\lambda)$ and I $2(\lambda)$ of sample illumination i.e. the light fluxes LA and LB by the Equations (19) and (20), respectively (Step S19). Then, the controller 7 calculates fluorescent spectral radiance factors $F1(\lambda)$ and $F2(\lambda)$ by the light fluxes LA and LB i.e. the illuminations I 1 and I 2 by the following Equations (26) and (27), based on the spectral intensities I $1(\lambda)$ and I $2(\lambda)$ i.e. the spectral intensities I $1(\lambda)$ and I $2(\lambda)$, and the bi-spectral luminescent radiance factor $F(\mu,\lambda)$ (Step S20).

$$F1(\lambda) = \int F(\mu,\lambda) \cdot I1(\mu) d\mu / I1(\lambda) \quad (26)$$

$$F2(\lambda) = \int F(\mu,\lambda) \cdot I2(\mu) d\mu / I2(\lambda) \quad (27)$$

Then, the controller 7 obtains a weighting factor $W(\lambda)$ by solving the following Equation (28), based on the calculated fluorescent spectral radiance factors $F1(\lambda)$ and $F2(\lambda)$, and the fluorescent spectral radiance factor $Fs(\lambda)$ obtained in Step S18, at each wavelength (Step S21).

$$W(\lambda) \cdot F1(\lambda) + (1 - W(\lambda)) \cdot F2(\lambda) = Fs(\lambda) \quad (28)$$

Then, the controller 7 calculates the total spectral radiance factors $Bx1(\lambda)$ and $Bx2(\lambda)$ by the light fluxes LA and LB by using the Equations (23) and (24), based on $Mx1(\lambda)$ and $Mx2(\lambda)$, and $Sx1(\lambda)$ and $Sx2(\lambda)$ stored in Steps S14 and S16 (Step S22). Then, the controller 7 calculates a total spectral radiance factor $Bxs(\lambda)$ by test illumination by the Equation (29), based on the calculated $Bx1(\lambda)$ and $Bx2(\lambda)$, and the weighting factor $W(\lambda)$ calculated in Step S21 (Step S23).

$$Bxs(\lambda) = W(\lambda) \cdot Bx1(\lambda) + (1 - W(\lambda)) \cdot Bx2(\lambda) \quad (29)$$

(B) Spectral Radiance Factor of a Printed Surface on Paper Treated by FWA

[Principle of Measurement]

Figure 12A:
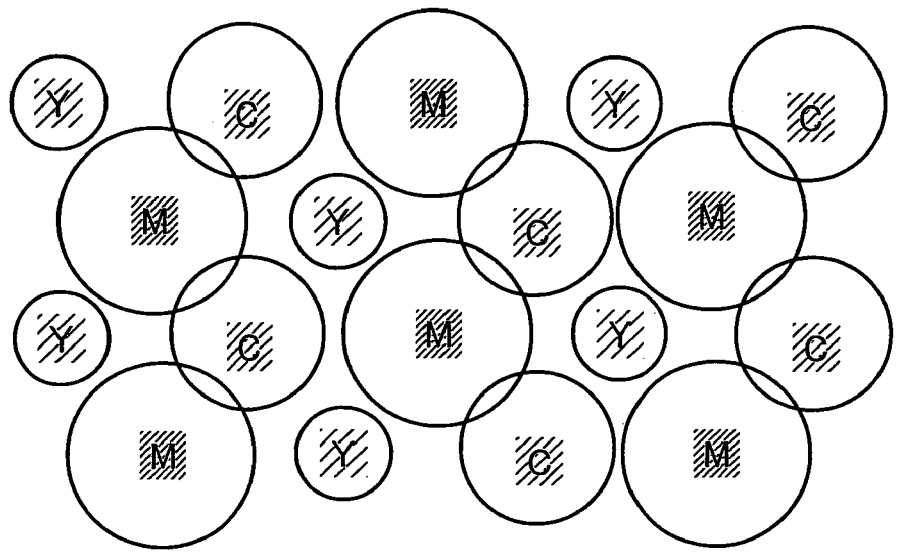
FIGS. 12A and 12B are conceptual diagrams for describing how ink dots of different colors are individually and superimposedly formed on FWA treated paper.
Figure 12B:
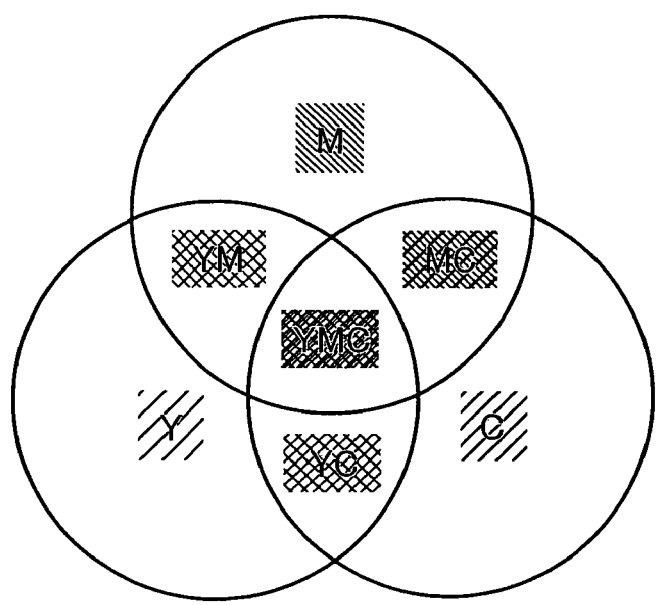

Generally, printed colors are made of a number of tiny dots of different sizes in four different inks i.e. Y (Yellow), M (Magenta), C (Cyan), and K (Black). Kink has a light absorption characteristic with no dependence on the wavelength, and accordingly, does not affect a relative spectral intensity of illumination light that reaches FWA treated paper. Therefore, as shown in FIG. 12A, in this example, the measurement principle is described based on Y, M, and C ink dots. For instance, as shown in FIG. 12B, there is a case that ink dots are superimposedly printed. A surface of FWA treated paper includes a printed area where Y, M, C, YM, MC, CY, and YMC ink dots are printed; and an unprinted area. Since the ink dots are printed on a surface of FWA treated paper in the aforementioned manner, spectral excitation of a measuring area depends on spectral transmittances of Y, M, C, YM, MC, CY, and YMC inks, and an area ratio of the printed area composed of dot areas of Y, M, C, YM, MC, CY, and YMC inks with respect to the measuring area, in other words, on colors.

Figure 2A:
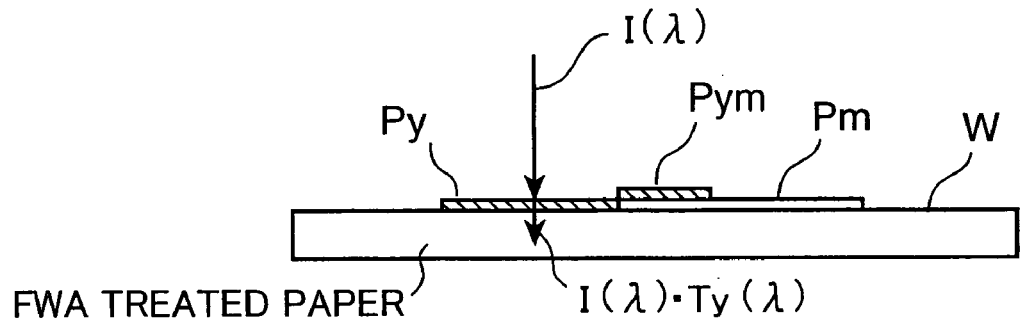
Figure 2B:
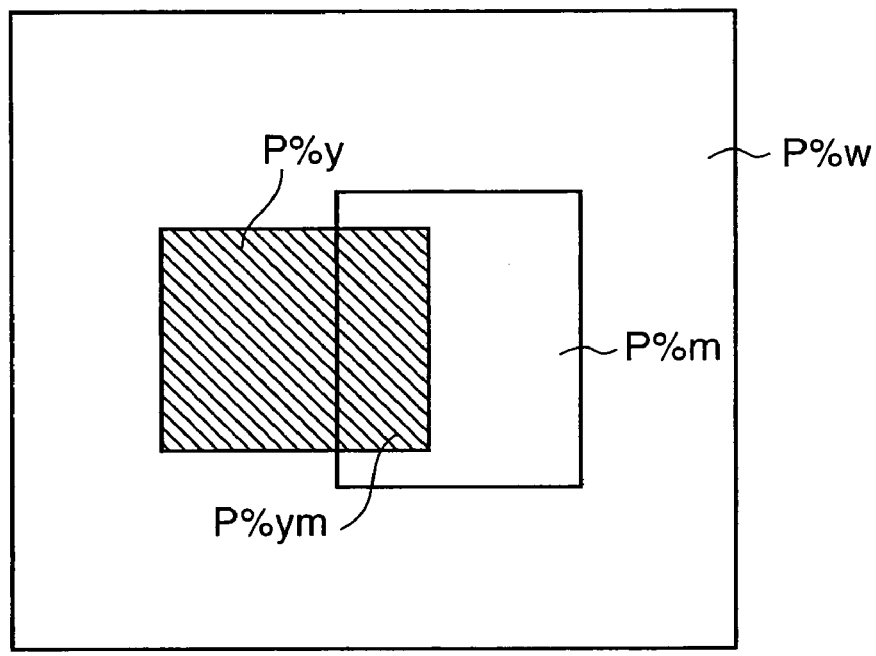

Now, an idea on how the ink dots are individually and superimposedly printed is described referring to FIGS. 2A and 2B. In this embodiment, a case of using Y ink and M ink among Y, M, and C inks is described. FIG. 2A is a cross-sectional view schematically showing a case that Y ink dots and M ink dots are printed on a surface of FWA treated paper. FIG. 2B is a top plan view of FIG. 2A showing the printed surface of FWA treated paper where Y ink dots and M ink dots are printed.

Assuming that a spectral intensity of illumination light per unit area is $I(\lambda)$, and spectral transmittances of Y ink and M ink are $Ty(\lambda)$ and $Tm(\lambda)$, respectively, $I(\lambda)$ directly reaches an unprinted area W on the FWA treated paper, but part of $I(\lambda)$ i.e. $I(\lambda) \cdot Ty(\lambda)$ reaches a yellow printed area Py composed merely of Y ink dots on the FWA treated paper. Similarly, spectral intensities of the incident illumination light $I(\lambda) \cdot Tm(\lambda)$ and $I(\lambda) \cdot Ty(\lambda) \cdot Tm(\lambda)$ reach a magenta printed area Pm composed merely of M ink dots, and a yellow-magenta printed area Pym where Y ink dots and M ink dots are superimposedly printed on the FWA treated paper, respectively.

Accordingly, a spectral intensity I e$(\lambda)$ (see the following Equation (30)) of effective illumination light that reaches the entirety of the measuring area of FWA treated paper per unit area is the sum of $I(\lambda) \cdot Ty(\lambda)$, $I(\lambda) \cdot Tm(\lambda)$, $I(\lambda) \cdot Ty(\lambda) \cdot Tm(\lambda)$, and $I(\lambda)$ weighted by the area ratios P % y, P % m, P % ym, and P % w(=1−(P % y+P % m+P % ym)) of the dot areas Py, Pm, Pym, and the unprinted area W shown in FIG. 2B.

$$Ie(\lambda)=[P\% \, y \cdot I(\lambda) \cdot Ty(\lambda)+P\% \, m \cdot I(\lambda) \cdot Tm(\lambda)+P\% \, ym \cdot I(\lambda) \cdot Ty(\lambda) \cdot Tm(\lambda)+P\% \, w \cdot I(\lambda)] \quad (30)$$

Based on the above Equation (2), the spectral intensity F(λ) of fluorescent light excited by the illumination light is derived from the following Equation (31).

$$F(\lambda) = \int Ie(\mu) \cdot F(\mu, \lambda) d\mu \quad (31)$$
$$= I(\lambda) \cdot [P\% \, y \cdot Ty(\mu) + P\% \, m \cdot Tm(\mu) + P\% \, ym \cdot Ty(\mu) \cdot Tm(\mu) + P\% \, w] \cdot F(\mu, \lambda)$$

On the other hand, assuming that the term: [P % y·Ty(μ)+P % m·Tm(μ)+P % ym·Ty(μ)·Tm(μ)+P % w]·F(μ,λ) in the right side of the Equation (31) is an effective bi-spectral luminescent radiance factor Fe(μ,λ), the spectral intensity F(λ) of fluorescent light is expressed by the following Equation (32).

$$F(\lambda) = \int I(\mu) \cdot Fe(\mu,\lambda) d\mu \quad (32)$$

Now, the number of kinds of ink is increased from two kinds i.e. Y ink and M ink to all the four kinds of inks i.e. Y, M, C, and K inks to be used in actual colorimetry. Similarly to the above description, assuming that area ratios of dot areas where Y, M, C, and K ink dots are individually and superimposedly printed, which are represented by y, m, c, ym, mc, cy, ymc, and k, are P % y, P % m, P % c, P % ym, P % mc, P % cy, P % ymc, and P % k, the area ratios of dot areas are calculated by a well-known method based on an actually measured total spectral radiance factor obtained by illuminating the FWA treated paper with illumination light from the first illuminator 2 having the incandescent lamp 21 as a light source.

Since the incandescent lamp 21 has an extremely low relative ultraviolet intensity, area ratios obtained based on the actually measured total spectral radiance factor hardly include an error resulting from fluorescent light. Total spectral radiance factors Bw1(λ); and By1(λ), Bm1(λ), Bc1(λ), Bym1(λ), Bmc1(λ), Bcy1(λ), Bymc1(λ), and Bk1(λ) by the first illuminator 2 with respect to the unprinted area; and whole printed surfaces i.e. reference printed surfaces where the ink dots are individually and superimposedly printed each with the area ratio of 100%, are measured, as a reference for area ratio calculation, and stored in e.g. the BLRF storage 73.

An effective bi-spectral luminescent radiance factor Fe(μ,λ) on a printed surface to be measured is estimatively calculated by the following Equation (33), based on the area ratios P % y, P % m, P % c, P % ym, P % mc, P % cy, P % ymc, and P % k of the dot areas, which have been calculated by the well-known method; an area ratio P % w=1−Σ P % (ΣP % is the sum of area ratios of all the dot areas) of the unprinted area W; the predefined and stored bi-spectral luminescent radiance factor (μ,λ) of the FWA treated paper; and the spectral transmittances Ty(λ), Tm(λ), and Tc(λ) of the inks. The spectral transmittances Ty(λ), Tm(λ), and Tc(λ) of the inks are also predefined and stored e.g. in the area ratio storage 75, and given as numerical data. K ink having a spectral transmittance with no dependence on the wavelength merely affects the area ratio P % w of the unprinted area W. Accordingly, K ink does not require processing as required in Y, M, and C inks.

$$Fe(\mu,\lambda)=[P\% \, y \cdot Ty(\mu)+P\% \, m \cdot Tm(\mu)+P\% \, c \cdot Tc(\mu)+P\% \, ym \cdot Ty(\mu) \cdot Tm(\mu)+P\% \, mc \cdot Tm(\mu) \cdot Tc(\mu)+P\% \, cy \cdot Tc(\mu) \cdot Ty(\mu)+P\% \, ymc \cdot Ty(\mu) \cdot Tm(\mu) \cdot Tc(\mu)+P\% \, w] \cdot F(\mu,\lambda) \quad (33)$$

In the above computation, the spectral transmittances Ty(λ), Tm(λ), Tc(λ), and Tymc(λ) of combination of the inks are calculated by the product with the spectral transmittances Ty(λ), Tm(λ), and Tc(λ) of the inks. Alternatively, the spectral transmittances Ty(λ), Tm(λ), Tc(λ), and Tymc(λ) of combination of the inks may be predefined and stored (see the Equation (33′)).

$$Fe(\mu,\lambda)=[P\% \, y \cdot Ty(\mu)+P\% \, m \cdot Tm(\mu)+P\% \, c \cdot Tc(\mu)+P\% \, ym \cdot Tym(\mu)+P\% \, mc \cdot Tmc(\mu)+P\% \, cy \cdot Tcy(\mu)+P\% \, ymc \cdot Tymc(\mu)+P\% \, w] \cdot F(\mu,\lambda) \quad (33')$$

A total spectral radiance factor of the printed surface to be measured, which is obtained by illuminating the printed surface to be measured with the test illumination, is calculated based on the estimated effective bi-spectral luminescent radiance factor Fe(μ,λ) by a procedure similar to the aforementioned procedure used in measuring the factor (A).

Alternatively, the effective bi-spectral luminescent radiance factor Fe(μ,λ) (see the following Equation (34)) may be obtained, based on the area ratios of Y, M, C, and K ink dots, and predefined bi-spectral luminescent radiance factors Fy(μ,λ), Fm(μ,λ), Fc(μ,λ), Fym(μ,λ), Fmc(μ,λ), Fcy(μ,λ), and Fymc(μ,λ) of whole printed surfaces where the ink dots are individually and superimposedly printed each with an area ratio of 100%.

$$Fe(\mu,\lambda)=P\% \, y \cdot Fy(\lambda,\mu)+P\% \, m \cdot Fm(\mu,\lambda)+P\% \, c \cdot Fc(\lambda,\mu)+P\% \, ym \cdot Fym(\mu,\lambda)+P\% mc \cdot Fmc(\mu,\lambda)+P\% cy \cdot Fcy(\mu,\lambda)+P\% ymc \cdot Fymc(\mu,\lambda)+P\% w \cdot F(\mu,\lambda) \quad (34)$$

The spectral transmittances Ty(λ), Tm(λ), Tc(λ) of Y ink, M ink, and C ink, or the spectral transmittances Ty(λ), Tm(λ), Tc(λ), Tym(λ), Tmc(λ), Tcy(λ), and Tymc(λ) of the individual inks and combinations of the inks may be given in advance, as spectral transmittances of reference whole printed surfaces composed of ink layers of the individual inks and ink layers of the superimposed inks. The reference whole printed surfaces are substantially identical or approximate to the ink layers. However, even in use of the reference whole printed surfaces printed with the same inks, the ink layer thickness or the ink concentration may differ depending on a printing condition such as an ink lot, or an ambient temperature of a printing machine. As a result, the effective bi-spectral luminescent radiance factor Fe(μ,λ) obtained by using the spectral transmittance of the reference printed surface different in printing condition from the printed surface to be measured, or the total spectral radiance factor derived from the effective bi-spectral luminescent radiance factor Fe(μ,λ) may include a non-negligible measurement error. In the following, an example of an approach of precisely obtaining spectral transmittances Ty(λ), Tm(λ), Tc(λ), Tym(λ), Tmc(λ), Tcy(λ), and Tymc(λ) of the individual inks and combinations of the inks in conformity with the printing condition of a fluorescent sample to be measured is described.

As described above, if spectral transmittances of reference samples printed with individual inks and combinations of the inks each at an area ratio of 100% are measured in advance and directly used, a measurement error may occur in an effective bi-spectral luminescent radiance factor Fe(μ,λ) using the spectral transmittances, or a total spectral radiance factor Bt(μ,λ) derived based on Fe(μ,λ). It is obviously difficult to measure a spectral transmittance of an actual printed surface by the optical property measuring apparatus 10, and it is further unrealistic to measure the spectral transmittance including an ultraviolet region relating to excitation.

As described above, in the embodiment, the spectral transmittance characteristic of the reference sample is measured in advance including the ultraviolet region relating to excitation. The total spectral radiance factor by the light flux LA i.e. the illumination I 1 is measured in advance by a reference measuring apparatus having the same construction as the optical property measuring apparatus 10, and stored. Since the light flux LA hardly excites fluorescent light, the total spectral radiance factor is substantially a spectral reflection radiance factor. Then, a spectral transmittance of a whole printed surface, which is printed under the same printing condition as the printed surface to be measured, is obtained by correcting the spectral transmittance of the reference sample, based on a measurement value of spectral reflection radiance factor of the whole printed surface, and the stored spectral reflection radiance factor of the reference printed surface. This calculation is performed based on a finding that there is a fixed relation between the ink concentration or the ink layer thickness on a printed surface, and a transmittance and a reflection radiance factor.

Specifically, reference printed surfaces are obtained by printing Y, M, and C inks and combinations of these inks on a non-fluorescent substrate e.g. semi-transparent paper having a high transmittance by a printing machine. Spectral transmittances $Ty(\lambda)$, $Tm(\lambda)$, $Tc(\lambda)$, $Tym(\lambda)$, $Tmc(\lambda)$, $Tcy(\lambda)$, and $Tymc(\lambda)$ of the reference printed surfaces, and a spectral transmittance $Tw(\lambda)$ of a non-printed surface are measured by the reference measuring apparatus in a wavelength region from e.g. about 300 to 700 nm including an ultraviolet region. Then, $T0y(\lambda)(=Ty(\lambda)/Tw(\lambda))$, $T0m(\lambda)(=Tm(\lambda)/Tw(\lambda))$, $T0c(\lambda)(=Tc(\lambda)/Tw(\lambda))$, $T0ym(\lambda)(=Tym(\lambda)/Tw(\lambda))$, $T0mc(\lambda)(=Tmc(\lambda)/Tw(\lambda))$, $T0cy(\lambda)(=Tcy(\lambda)/Tw(\lambda))$, and $T0ymc(\lambda)(=Tymc(\lambda)/Tw(\lambda))$, which are obtained by calculating the spectral transmittances of the reference printed surfaces with respect to the spectral transmittance of the non-printed surface, are stored into e.g. the area ratio storage 75, as spectral transmittance reference values of the reference printed surfaces.

Further, spectral reflection radiance factors $By1(\lambda)$, $Bm1(\lambda)$, $Bc1(\lambda)$, $Bym1(\lambda)$, $Bmc1(\lambda)$, $Bcy1(\lambda)$, $Bymc1(\lambda)$, and $Bk1(\lambda)$ of the reference printed surfaces, and $Bw1(\lambda)$ of the non-printed surface in the wavelength region from about 400 to 700 nm excluding the ultraviolet region are measured by the light flux LA i.e. the illumination I 1 of the first illuminator 2 having the incandescent lamp 21 as a light source, by using the reference measuring apparatus or the optical property measuring apparatus 10.

Then, $R0y(\lambda)(=By1(\lambda)/Bw1(\lambda))$ $R0m(\lambda)(=Bm1(\lambda)/Bw1(\lambda))$, $R0c(\lambda)(=Bc1(\lambda)/Bw1(\lambda))$, $R0ym(\lambda)(=Bym1(\lambda)/Bw1(\lambda))$, $R0mc(\lambda)(=Bmc1(\lambda)/Bw1(\lambda))$, $R0cy(\lambda)(=Bcy1(\lambda)/Bw1(\lambda))$, $R0ymc(\lambda)(=Bymc1(\lambda)/Bw1(\lambda))$, and $B0k(\lambda)(=Bk1(\lambda)/Bw1(\lambda))$, which are obtained by calculating the spectral reflection radiance factors of the reference printed surfaces with respect to the spectral reflection radiance factor $Bw1(\lambda)$ of the non-printed surface, are stored into e.g. the area ratio storage 75, as spectral reflection radiance factor reference values of the reference printed surfaces in the similar manner as described above.

Prior to measurement of the printed surface to be measured, spectral reflection radiance factors of the whole printed surfaces where the individual inks and combinations of the inks are printed under the same printing condition as the printed surface to be measured, and of the non-printed surface in the wavelength region from about 400 to 700 nm, are measured by the light flux LA i.e. the illumination I 1 by the optical property measuring apparatus 10.

Similarly to the above, $Ry(\lambda)(=By1(\lambda)/Bw1(\lambda))$, $Rm(\lambda)(=Bm1(\lambda)/Bw1(\lambda))$, $Rc(\lambda)(=Bc1(\lambda)/Bw1(\lambda))$, $Rym(\lambda)(=Bym1(\lambda)/Bw1(\lambda))$, $Rmc(\lambda)(=Bmc1(\lambda)/Bw1(\lambda))$, $Rcy(\lambda)(=Bcy1(\lambda)/Bw1(\lambda))$, $Rymc(\lambda)(=Bymc1(\lambda)/Bw1(\lambda))$, and $Rk(\lambda)(=Bk1(\lambda)/Bw1(\lambda))$ are obtained by calculating the spectral reflection radiance factors of the whole printed surfaces with respect to the spectral reflection radiance factor $Bw1(\lambda)$ of the non-printed surface.

Figure 13:
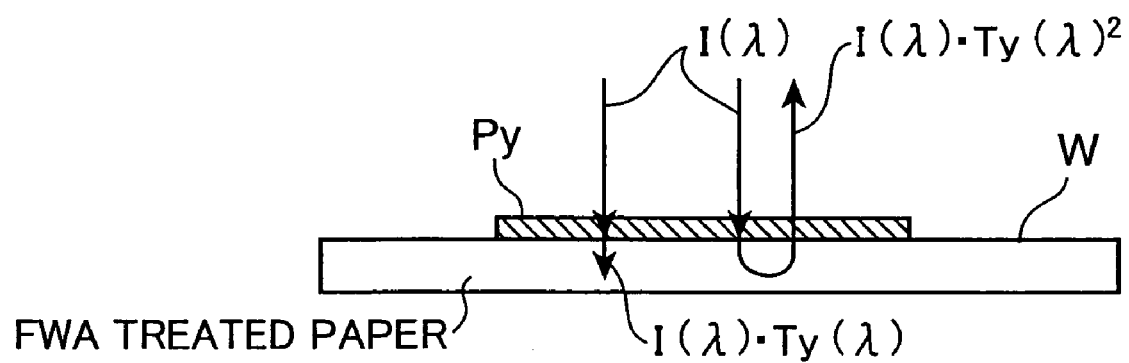
FIG. 13 is a conceptual diagram for describing an influence of an ink on FWA treated paper to transmitted light and reflecting light.

As shown in FIG. 13, transmitted light transmits an ink layer once, and reflecting light transmits the ink layer twice. Therefore, the following Equation (35) is established between the reflectance R and the transmittance T of each ink layer.

$$R \approx T^2 \quad (35)$$

In the case where the spectral reflection radiance factor $R(\lambda)$ of the printed surface to be measured, and the spectral reflection radiance factor $R0(\lambda)$ of the reference printed surface are different resulting from a difference in ink layer thickness, a difference in ink concentration, or a like factor, the spectral transmittance ratio of the printed surface to be measured relative to the reference printed surface can be approximated by an approximate value: $(R(\lambda)/R0(\lambda))1/2$, based on the above relation (35). An estimated spectral transmittance $T(\lambda)$ of the printed surface to be measured is given by the following Equation (36), wherein the spectral transmittance $T0(\lambda)$ of the reference printed surface is corrected by the approximate value of the spectral transmittance ratio i.e. $(R(\lambda)/R0(\lambda))1/2$. In the following Equation (39), $T(\lambda)$ and $R(\lambda)$ in the Equation (36) are substituted by $Ty(\lambda)$ and $Ry(\lambda)$ in the case where Y ink is used.

$$T(\lambda) = (R(\lambda)/R0(\lambda))^{1/2} \cdot T0(\lambda) \quad (36)$$

The spectral reflection radiance factors $R(\lambda)$ and $R0(\lambda)$ cannot be measured in a wavelength region smaller than 400 nm. In this example, a non-measurable wavelength region is an ultraviolet region from 300 to 390 nm, if the wavelength region from 300 to 700 nm is divided into a wavelength region from 300 to 390 nm, and a wavelength region from 400 nm to 700 nm. In other words, $R(\lambda)$ and $R0(\lambda)$ cannot be measured in the non-measurable wavelength region where a spectral reflection characteristic is not derived. However, the spectral reflection characteristic in the non-measurable wavelength region can be substituted by a reflection radiance factor in a wavelength region including a wavelength at a measurable short-wavelength end or a wavelength near the measurable short-wavelength, in other words, an adjacent wavelength region, which is adjacent to the non-measurable wavelength region, in the measurable wavelength region where a spectral reflection characteristic is derived.

As described above, an average spectral transmittance characteristic of a colored surface i.e. a measuring area can be calculated, based on the calculated spectral transmittances $T(\lambda)$ of the whole printed surfaces where the individual inks and combinations of the inks are printed each with an area ratio of 100%, and the area ratios P % m, P % c, P % ym, P % mc, P % cy, P % ymc, and P % k of the individual inks and the combinations of the inks. The average spectral transmittance characteristic depends on the spectral transmittance characteristics of the whole printed areas where the individual inks and the combinations of the inks are printed, and the area ratios of the individual inks and the combinations of the inks within the measuring area. Accordingly, spectral excitation-fluorescence characteristics of the measuring area depend on the spectral transmittances of the whole printed surfaces, and the area ratios within the measuring area.

The aforementioned measurement principle on the spectral radiance factor of the printed surface on FWA treated paper can also be summarized as follows.

b1. An effective bi-spectral luminescent radiance factor of a printed surface on a fluorescent substrate is estimated based on a bi-spectral luminescent radiance factor of the fluorescent substrate, and spectral transmittance characteristics and area ratios of individual inks and combinations of the inks.

b2. The items a1 through a4 in the measurement principle on the total spectral radiance factor to be obtained in the case where the sample is illuminated with the test illumination are applied to the estimated effective bi-spectral luminescent radiance factor.

b3. The area ratios of the individual inks and the combinations of the inks are estimated based on an actually measured total spectral radiance factor by illumination light substantially having no excitation energy, in other words, substantially free of an influence of fluorescent light.

<Measurement Procedure on the Total Spectral Radiance Factor of the Printed Surface of FWA Treated Paper>

Figure 5:
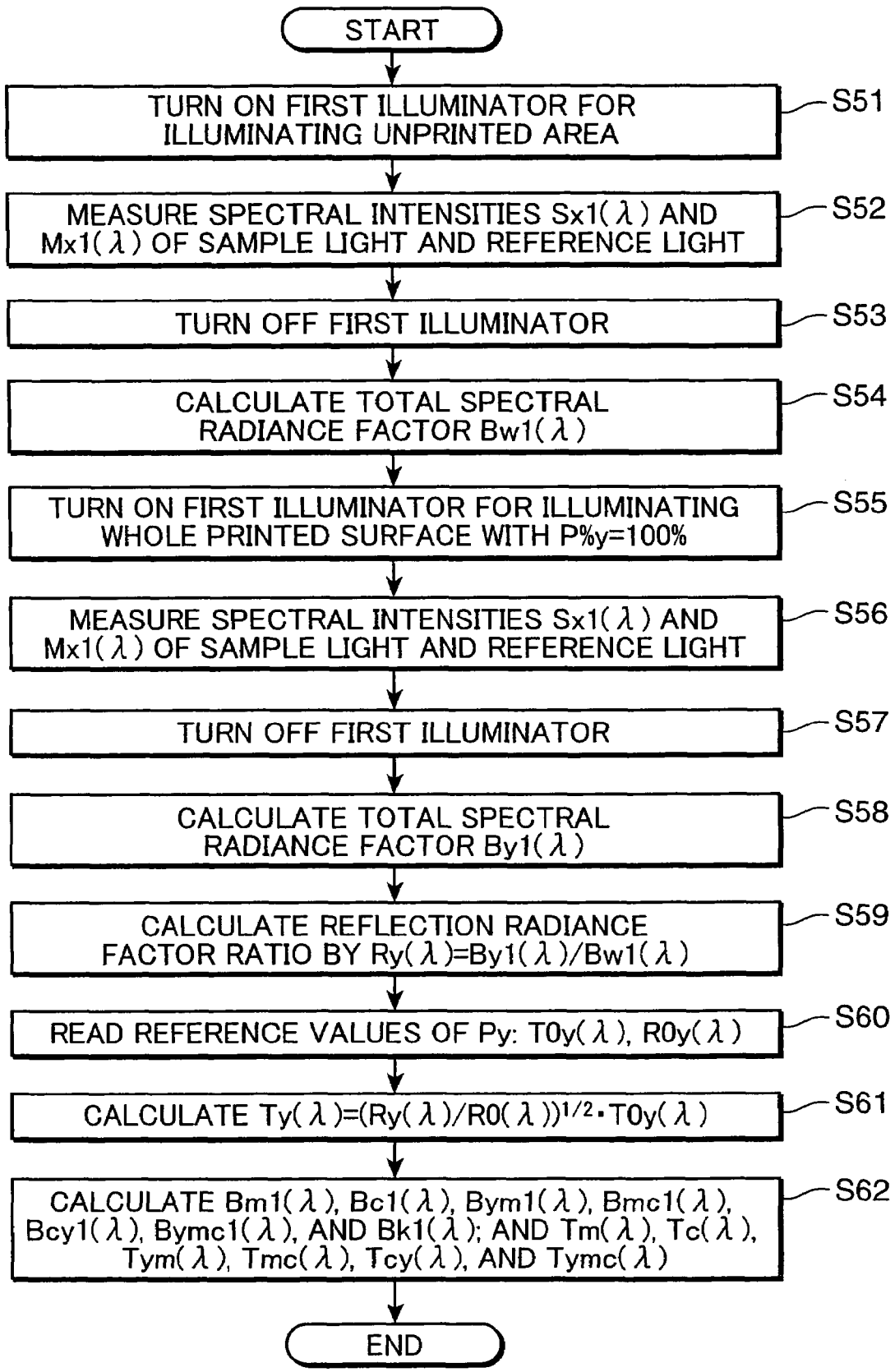
FIG. 5 is a flowchart for measuring a whole printed surface with an ink area ratio of 100%.
Figure 6A:
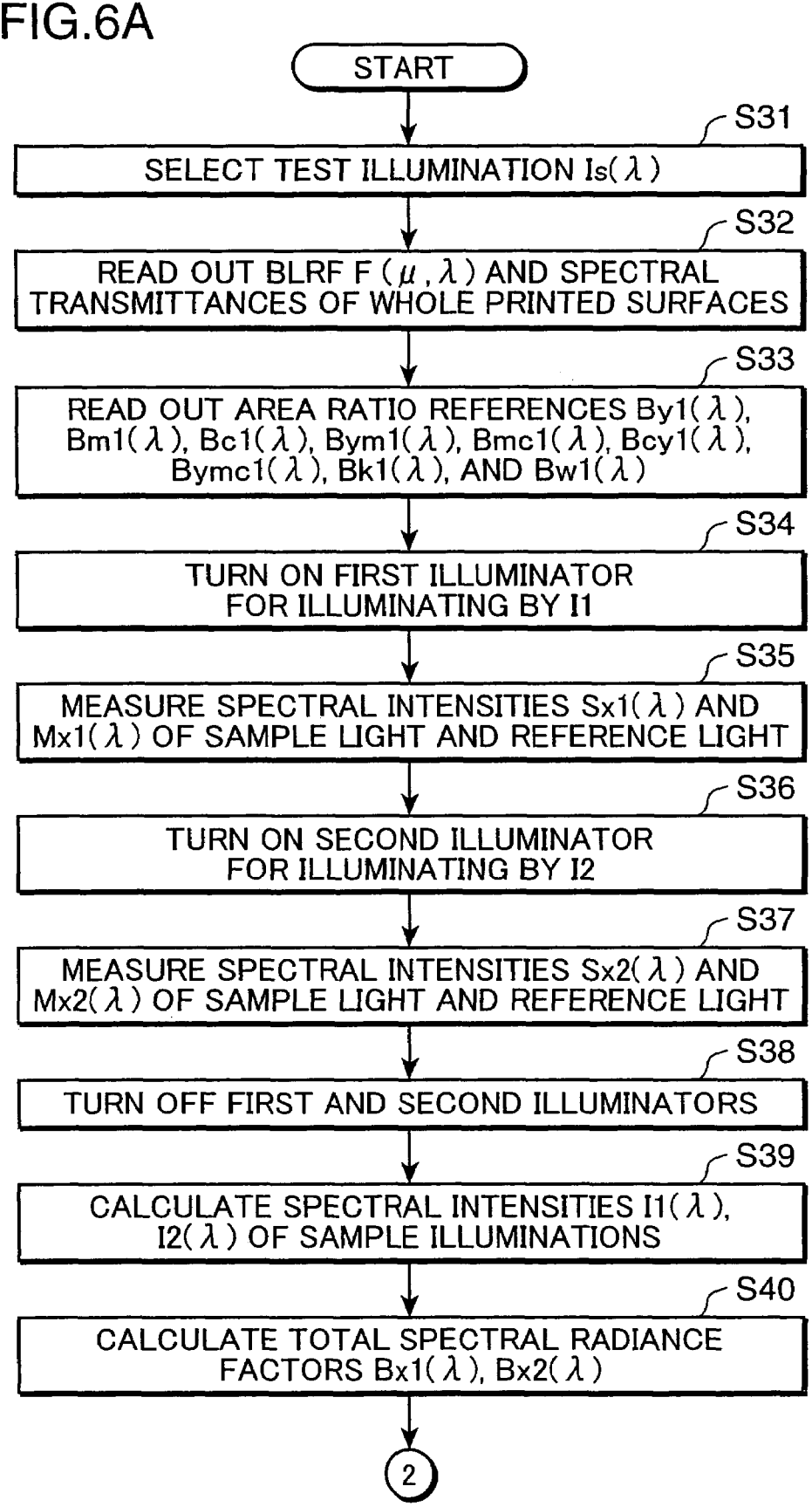
FIGS. 6A and 6B are a flowchart for measuring a total spectral radiance factor of a surface of FWA treated paper by the optical property measuring apparatus.
Figure 6B:
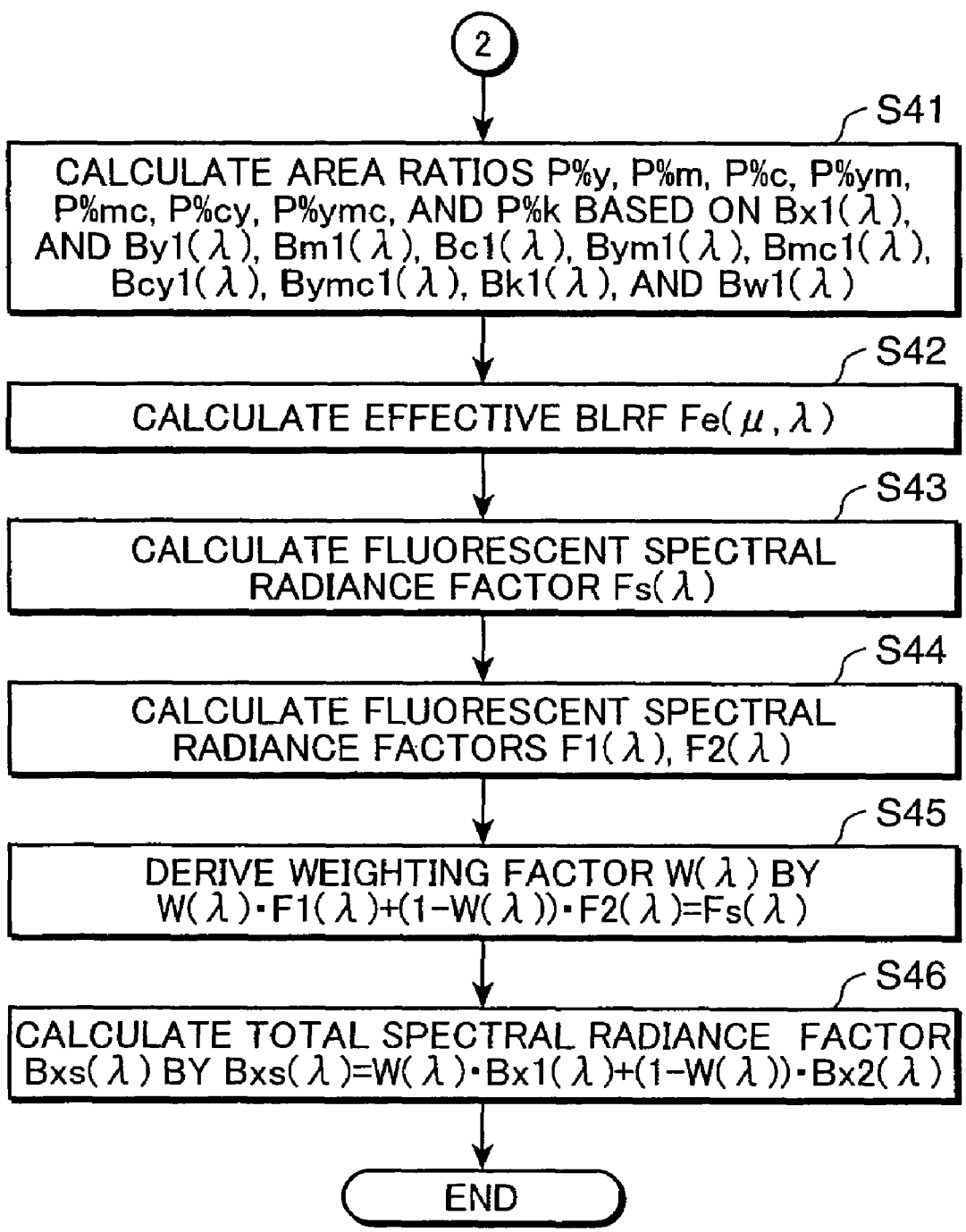
Figure 7:
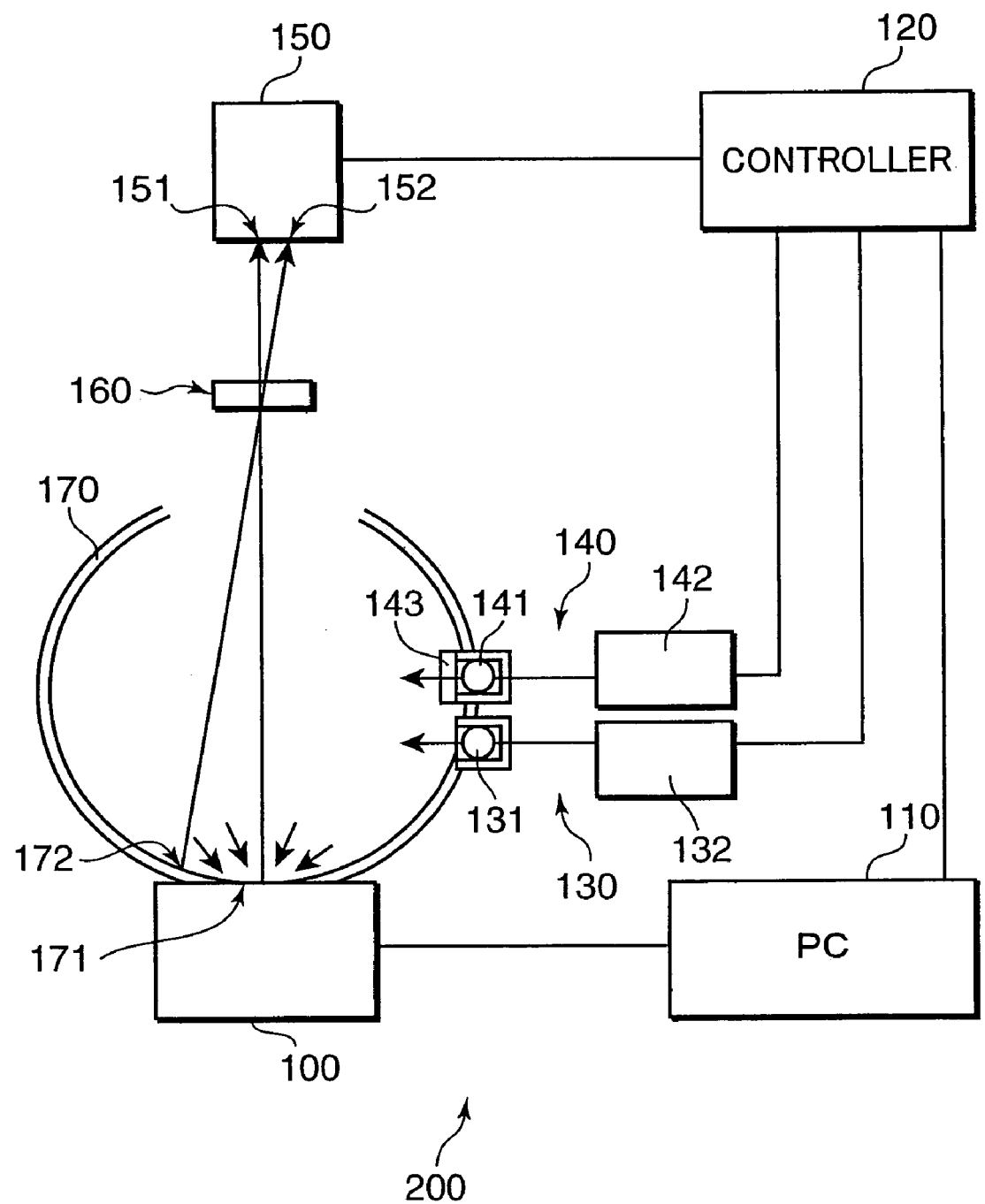
FIG. 7 is a schematic diagram showing an arrangement that the measuring method of the embodiment is applied to a conventional measuring apparatus.
Figure 8:
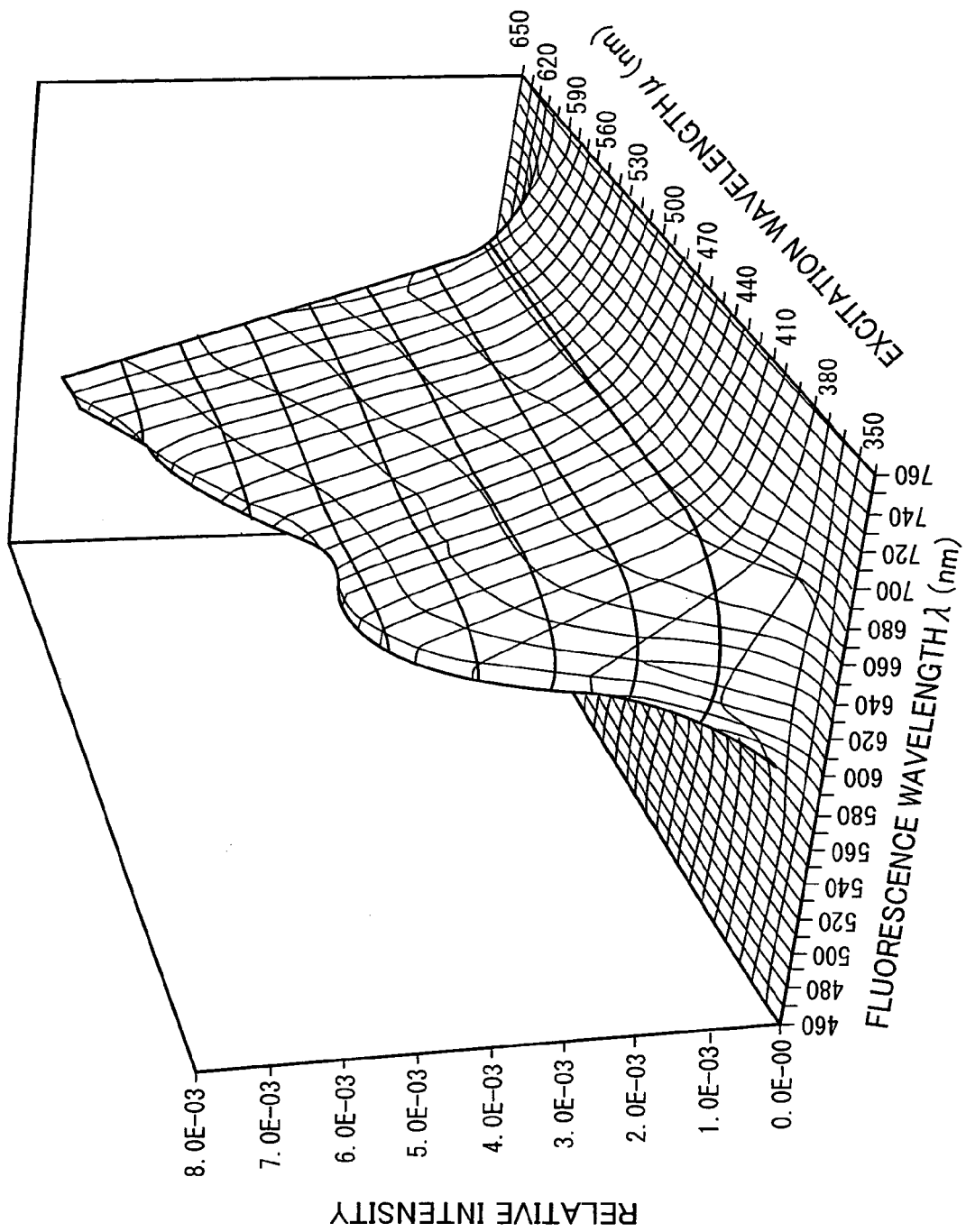
FIG. 8 is a graph showing matrix data on an intensity of a bi-spectral luminescent radiance factor.

The total spectral radiance factor of the printed surface of FWA treated paper as a fluorescent sample is measured by the optical property measuring apparatus 10 in such a manner that whole printed surfaces and a non-printed surface are measured according to a flowchart shown in FIG. 5, and then, a printed surface to be measured is measured according to a flowchart shown in FIGS. 6A and 6B.

FIG. 5 is a flowchart showing an example of measuring a whole printed surface. After the white calibration is performed according to the flowchart shown in FIG. 3, first, the incandescent lamp 21 of the first illuminator 2 is turned on to illuminate a non-printed surface i.e. FWA treated paper disposed in the measurement aperture with the light flux LA i.e. the illumination I 1 (Step S51). Then, the dual channel spectral unit 6 as the spectral measuring unit measures the spectral intensity $Sx1(\lambda)$ of sample light by the light flux LA and the spectral intensity $Mx1(\lambda)$ of reference light by the light flux LA, and the spectral intensity information on $Sx1(\lambda)$ and $Mx1(\lambda)$ is stored in the spectral intensity storage 71 (Step S52). Then, the first illuminator 2 is turned off (Step S53).

Then, a total spectral radiance factor $Bw1(\lambda)$ of the non-printed surface illuminated with the light flux LA is calculated by the following Equation (37) corresponding to the Equation (23), based on $Sx1(\lambda)$ and $Mx1(\lambda)$ stored in Step S52, and is stored into a predetermined storage e.g. the area ratio storage 75 (Step S54).

$$Bw1(\lambda)=C1(\lambda)\cdot Sx1(\lambda)/Mx1(\lambda) \quad (37)$$

Then, the first illuminator 2 is turned on to illuminate a whole printed surface where Y ink is printed with an area ratio of P % y=100% with the light flux LA i.e. the illumination I 1 (Step S55). Then, the dual channel spectral unit 6 as the spectral measuring unit measures the spectral intensity $Sx1(\lambda)$ of sample light by the light flux LA and the spectral intensity $Mx1(\lambda)$ of reference light by the light flux LA, and the spectral intensity information on $Sx1(\lambda)$ and $Mx1(\lambda)$ is stored into the spectral intensity storage 71 (Step S56). Then, the first illuminator 2 is turned off (Step S57).

Then, similarly to Step S54, a total spectral radiance factor $By1(\lambda)$ of the Y-ink whole printed surface obtained by illumination with the light flux LA is calculated based on $Sx1(\lambda)$ and $Mx1(\lambda)$ stored in Step S56, and stored into the predetermined storage e.g. the area ratio storage 75 (Step S58).

Then, a spectral reflection radiance factor $Ry(\lambda)$ of the Y-ink whole printed surface obtained by calculation with respect to the total spectral radiance factor of the non-printed surface, is obtained by the following Equation (38) (Step S59).

$$Ry(\lambda)=By1(\lambda)/Bw1(\lambda) \quad (38)$$

Then, the spectral transmittance reference value $T0y(\lambda)$ of the Y-ink reference whole printed surface, and the spectral reflection radiance factor reference value $R0y(\lambda)$ obtained by the above computation are read from the area ratio storage 75 (Step S60). Then, a spectral transmittance $Ty(\lambda)$ of the Y-ink whole printed surface is obtained by the following Equation (39).

$$Ty(\lambda)=(Ry(\lambda)/R0y(\lambda))^{1/2}\cdot T0y(\lambda) \quad (39)$$

The measurable wavelength region of the total spectral radiance factor is from 400 to 700 nm, and there is no actual measurement value for $Ry1(\lambda)$ and $R0y(\lambda)$ in the wavelength region from 300 to 390 nm. Accordingly, $Ry1(400)$ and $R0y(400)$ where the wavelength $\lambda$ is 400 nm are used as $Ry1(\lambda)$ and $R0y(\lambda)$ in the wavelength region from 300 to 390 nm.

Similarly to the above, the operations from Steps S51 through S61 are repeated with respect to whole printed surfaces with the area ratios P % m, P % c, P % ym, P % mc, P % cy, P % ymc, and P % k. Total spectral radiance factors $Bm1(\lambda)$, $Bc1(\lambda)$, $Bym1(\lambda)$, $Bmc1(\lambda)$, $Bcy1(\lambda)$, $Bymc1(\lambda)$, and $Bk1(\lambda)$, and the spectral transmittances $Tm(\lambda)$, $Tc(\lambda)$, $Tym(\lambda)$, $Tmc(\lambda)$, $Tcy(\lambda)$, and $Tymc(\lambda)$ are calculated, and stored in e.g. the area ratio storage 75 (Step S62).

FIGS. 6A and 6B are a flowchart showing an example of measuring the total spectral radiance factor of the printed surface of FWA treated paper by the optical property measuring apparatus 10. First, test illumination I s is selected prior to measurement. Specifically, the controller 7 reads, from the test illumination storage 72, the spectral intensity data I $s(\lambda)$ i.e. the spectral intensity I $s(\mu)$ of the test illumination I s to be selected (Step S31). Then, the controller 7 selects the type of printing paper, and a set of Y, M, C, and K inks. Specifically, the controller 7 reads, from the BLRF storage 73 or the area ratio storage 75, data on the bi-spectral luminescent radiance factor $F(\mu,\lambda)$ approximate to that of printing paper i.e. FWA treated paper having a printed surface to be measured, and the spectral transmittances $Ty(\lambda)$, $Tm(\lambda)$, $Tc(\lambda)$, $Tym(\lambda)$, $Tmc(\lambda)$, $Tcy(\lambda)$, and $Tymc(\lambda)$ of ink layers on the whole printed surfaces where the individual inks of Y, M, C, and K and combinations of the inks are printed under the same printing condition as the printed surface to be measured (Step S32). Then, the controller 7 reads, from the area ratio storage 75, data on the total spectral radiance factors $By1(\lambda)$, $Bm1(\lambda)$ $Bc1(\lambda)$, $Bym1(\lambda)$, $Bmc1(\lambda)$, $Bcy1(\lambda)$, $Bymc1(\lambda)$, $Bk1(\lambda)$, and $Bw1(\lambda)$ as a reference for area ratio calculation. The total spectral radiance factors $By1(\lambda)$, $Bm1(\lambda)$, $Bc1(\lambda)$, $Bym1(\lambda)$, $Bmc1(\lambda)$, $Bcy1(\lambda)$, $Bymc1(\lambda)$, $Bk1(\lambda)$, and $Bw1(\lambda)$ are measured and stored by illuminating the whole printed surfaces, as area ratio references, where the individual inks of Y, M, C, and K, and the combinations of the inks are printed, by the first illuminator 2 (Step S33).

Then, the controller 7 turns on the incandescent lamp 21 of the first illuminator 2 to illuminate the sample 1 (in this example, the FWA treated paper having the printed surface to be measured) disposed in the measurement aperture with the light flux LA i.e. the illumination I 1 (Step S34). Then, the controller 7 causes the dual channel spectral unit 6 as the spectral measuring unit to measure the spectral intensity $Sx1(\lambda)$ of sample light by the light flux LA and the spectral intensity $Mx1(\lambda)$ of reference light by the light flux LA, and the spectral intensity information on $Sx1(\lambda)$ and $Mx1(\lambda)$ is stored into the spectral intensity storage 71 (Step S35). Then, the controller 7 turns on the ultraviolet LEDs 31 of the second illuminator 3 in a state that the on-state of the first illuminator 2 in Step S34 is maintained to illuminate the sample 1 with the light flux LB i.e. the illumination I 2 by the first illuminator 2 and the second illuminator 3 (Step S36). Then, similarly to Step S35, the controller 7 causes the dual channel spectral unit 6 to measure the spectral intensity $Sx2(\lambda)$ of sample light by the light flux LB, and the spectral intensity $Mx2(\lambda)$ of reference light by the light flux LB, and the spectral intensity information on Sx2(λ) and Mx2(λ) is stored into the spectral intensity storage 71 (Step S37). Then, the controller 7 turns off the first illuminator 2 and the second illuminator 3 (Step S38).

Then, the controller 7 converts the spectral intensities Mx1(λ) and Mx2(λ) of reference light by the light fluxes LA and LB into the spectral intensities I 1(λ) and I 2(λ) of sample illumination i.e. the light fluxes LA and LB by the Equations (19) and (20), respectively (Step S39). Data on the spectral intensities I 1(λ) and I 2(λ) obtained by the conversion is stored into the predetermined storage e.g. the spectral intensity storage 71. Then, the controller 7 calculates total spectral radiance factors Bx1(λ) and Bx2(λ) by the light fluxes LA and LB, by using the Equations (23) and (24), based on Sx1(λ), Mx1(λ), and Sx2(λ), Mx2(λ) stored in Steps S35, and S37, respectively (Step S40).

Then, the controller 7 calculates area ratios P % y, P % m, P % c, P % ym, P % mc, P % cy, P % ymc, and P % k of the dot areas where the individual inks of Y, M, C, and K and the combinations of the inks are printed, based on the calculated Bx1(λ), and the total spectral radiance factors By1(λ), Bm1(λ), Bc1(λ), Bym1(λ), Bmc1(λ), Bcy1(λ), Bymc1(λ), Bk1(λ), and Bw1(λ) of the area ratio references read out in Step S33. Then, the controller 7 calculates an effective bi-spectral luminescent radiance factor Fe(μ,λ) of the sample 1 by the Equation (33'), based on the calculated P % y, P % m, P % c, P % ym, P % mc, P % cy, P % ymc, and P % k, and the bi-spectral luminescent radiance factor F(μ,λ) and the spectral transmittances Ty(λ), Tm(λ), Tc(λ), Tym(λ), Tmc(λ), Tcy(λ), and Tymc(λ) of the ink layers on the whole printed surfaces, which have been read out in Step S32 (Step S42). Then, the controller 7 calculates a fluorescent spectral radiance factor Fs(λ) by the test illumination by the following Equation (40), based on the calculated effective bi-spectral luminescent radiance factor Fe(μ,λ), and the spectral intensity Is(λ) of the test illumination I s read out from the test illumination storage 72 in Step S31 (Step S43).

$$Fs(\lambda)=\int Fe(\mu,\lambda)\cdot Is(\mu)d\mu/Is(\lambda) \quad (40)$$

Then, the controller 7 calculates fluorescent spectral radiance factors F1(λ) and F2(λ) by the light fluxes LA and LB i.e. the illuminations I 1 and I 2 by the following Equations (41) and (42), respectively, based on the calculated fluorescent spectral radiance factor Fe(μ,λ), and the spectral intensities I 1(λ) and I 2(λ) read out from the spectral intensity storage 71 in Step S39 (Step S44).

$$F1(\lambda)=\int Fe(\mu,\lambda)\cdot I1(\mu)d\mu/I1(\lambda) \quad (41)$$

$$F2(\lambda)=\int Fe(\mu,\lambda)\cdot I2(\mu)d\mu/I2(\lambda) \quad (42)$$

Then, the controller 7 obtains a weighting factor W(λ) by solving the following Equation (43) by using the calculated fluorescent spectral radiance factors F1(λ) and F2(λ), and the fluorescent spectral radiance factor Fs(λ) obtained in Step S43 (Step S45).

$$W(\lambda)\cdot F1(\lambda)+[1-W(\lambda)]F2(\lambda)=Fs(\lambda) \quad (43)$$

Then, the controller 7 calculates a total spectral radiance factor Bxs(λ) by test illumination by the following Equation (44), based on the total spectral radiance factors Bx1(λ) and Bx2(λ) calculated in Step S40, and the weighting factor W(λ) calculated in Step S45 (Step S46).

$$Bxs(\lambda)=W(\lambda)\cdot Bx1(\lambda)+(1-W(\lambda))\cdot Bx2(\lambda) \quad (44)$$

As described above, the optical property measuring method of the embodiment is an optical property measuring method for calculating a spectral transmittance characteristic of an ink layer i.e. a colored layer composed of an ink or a colorant of a single kind, or inks or colorants of different kinds, or combination of the inks or the colorants by using a spectral reflection characteristic of the ink layer. The method comprises: a first step of acquiring or storing a spectral transmittance characteristic T0(λ) and a spectral reflection characteristic R0(λ) of a reference ink layer i.e. a reference colored layer or a reference printed surface defined as a reference, which is substantially identical or approximate to the corresponding ink layer; a second step of measuring or calculating a spectral reflection characteristic R(λ) of the corresponding ink layer based on optical measurement information of the ink layer e.g. the spectral intensity Sx1(λ) of sample light and the spectral intensity Mx1(λ) of reference light in Steps S55 and S56 shown in FIG. 5; and a third step of correcting the spectral transmittance characteristic T0(λ) of the reference ink layer based on the spectral reflection characteristic R(λ) of the ink layer and the spectral reflection characteristic R0(λ) of the reference ink layer to calculate a spectral transmittance characteristic T(λ) of the ink layer.

The optical property measuring apparatus 10 of the embodiment is an optical property measuring apparatus for calculating a spectral transmittance characteristic of an ink layer composed of an ink of a single kind, inks of different kinds, or combination of the inks, by using a spectral reflection characteristic of the ink layer. The apparatus comprises: a storing section such as the spectral intensity storage 71 or the area ratio storage 75 for storing an acquired spectral transmittance characteristic T0(λ) and an acquired spectral reflection characteristic R0(λ) of a reference ink layer defined as a reference, which is substantially identical or approximate to the corresponding ink layer; the CPU 70 in the controller 7, as a measuring or calculating section, for measuring or calculating a spectral reflection characteristic R(λ) of the ink layer based on optical measurement information of the ink layer e.g. based on Sx1(λ) and Mx1(λ). Then, the CPU 70 in the controller 7, as a correcting section, corrects the spectral transmittance characteristic T0(λ) of the reference ink layer based on the spectral reflection characteristic R(λ) of the ink layer and the spectral reflection characteristic R0(λ) of the reference ink layer to calculate a spectral transmittance characteristic T(λ) of the ink layer.

In the optical property measuring method or the optical property measuring apparatus of the embodiment, the spectral transmittance characteristics of the respective ink layers are calculated by correcting the acquired spectral transmittance characteristic of the reference ink layer, based on the acquired spectral reflection characteristic of the reference ink layer and the spectral reflection characteristic of the corresponding ink layer which has been measured or calculated based on the optical measurement information. In other words, the spectral transmittance characteristics of the respective ink layers are estimatively obtained by using the acquired spectral transmittance characteristic of the reference ink layer, based on the acquired spectral reflection characteristic of the reference ink layer and the spectral reflection characteristic of the corresponding ink layer which has been measured or calculated based on the optical measurement information. Accordingly, information on the spectral transmittance characteristics of the respective ink layers can be obtained with sufficient precision in conformity with a printing condition of a printed sample to be measured i.e. a printed status of FWA treated paper resulting from a difference in printing machine, ink lot, ambient temperature, or a like factor, in other words, an ink layer thickness difference, an ink concentration difference, or a like factor. Even if the spectral transmittance characteristics of the respective ink layers are varied by an ink layer thickness difference or an ink concentration difference resulting from a difference in printing machine, ambient temperature, or a like factor, the spectral transmittance characteristic of the corresponding ink layer can be precisely obtained. Thereby, colorimetry of the printed color of the printed sample i.e. a colored surface on a fluorescent substrate can be accurately performed.

Further, the spectral transmittance characteristic includes a spectral transmittance characteristic in a measurable wavelength region where a spectral reflection characteristic is derived, and a non-measurable wavelength region where a spectral reflection characteristic is not derived. The third step is a step of correcting the spectral transmittance characteristic of the reference ink layer, based on the spectral reflection characteristics of the respective ink layers and the spectral reflection characteristic of the reference ink layer in the measurable wavelength region, if the wavelength to be measured is in the measurable wavelength region, and based on the spectral reflection characteristics of the respective ink layers and the spectral reflection characteristic of the reference colored layer in an adjacent wavelength region in the measurable wavelength region, the adjacent wavelength region being adjacent the non-measurable wavelength region, if the wavelength to be measured is in the non-measurable wavelength region.

In the above arrangement, the spectral transmittance characteristics of the respective reference ink layers are corrected, based on the spectral reflection characteristics of the corresponding ink layer and the reference ink layer, if the wavelength to be measured is in the measurable wavelength region e.g. from 400 to 700 nm, and are corrected based on the spectral reflection characteristics of the corresponding ink layer and the reference ink layer in the adjacent wavelength region, which is adjacent the non-measurable wavelength region, in the measurable wavelength region, if the wavelength to be measured is in the non-measurable wavelength region i.e. an ultraviolet region smaller than 400 nm e.g. from 300 to 390 nm. In correcting the spectral transmittance characteristic of the corresponding reference ink layer, the spectral reflection characteristic in the adjacent wavelength region in the measurable wavelength region where a spectral reflection characteristic is derived can be used for measurement in the non-measurable wavelength region where an actual measurement value of a spectral reflection characteristic is not derived. Thereby, the spectral transmittance characteristics of the respective reference ink layers in the measurable wavelength region and the non-measurable wavelength region can be easily corrected.

Further, the optical property measuring method is a method for calculating a spectral transmittance characteristic of a colored surface on a fluorescent substrate. The colored surface is composed of an ink of a single kind, inks of different kinds, or combination of the inks. The third step is a step of calculating an average spectral transmittance characteristic of the colored surface, based on the spectral transmittance characteristics of the respective ink layers which have been calculated based on the optical measurement information, and an area ratio of the ink of the single kind, the inks of the different kinds, or the combination of the inks.

In the above arrangement, the average spectral transmittance characteristic of the colored surface is calculated based on the calculated spectral transmittance characteristics of the respective ink layers, and the area ratio of the ink of the single kind, the inks of the different kinds, or the combination of the inks. Even if the spectral transmittance characteristic of the colored surface is varied by an ink layer thickness difference or an ink concentration difference resulting from a difference in printing machine, ambient temperature, or a like factor, the average spectral transmittance characteristic of the colored surface can be precisely obtained.

Further, the optical property measuring method is a method for calculating excitation-fluorescence characteristics of the colored surface on the fluorescent substrate. The colored surface is composed of an ink of a single kind, inks of different kinds, or combination of the ink. The optical property measuring method further comprises a step of calculating effective excitation-fluorescence characteristics of the colored surface based on the calculated average spectral transmittance characteristic and excitation-fluorescence characteristics of the fluorescent substrate.

In the above arrangement, the effective excitation-fluorescence characteristics of the colored surface are calculated based on the calculated average spectral transmittance characteristic and the excitation-fluorescence characteristics of the fluorescent substrate. In this arrangement, even if the spectral transmittance characteristic of the colored surface is varied by an ink layer thickness difference or an ink concentration difference resulting from a difference in printing machine, ambient temperature, or a like factor, the effective excitation-fluorescence characteristics of the colored surface can be precisely obtained.

Further, the spectral transmittance characteristic is a spectral transmittance, and the spectral reflection characteristic is a spectral reflection radiance factor. This arrangement enables to obtain the average spectral transmittance of the colored surface on the fluorescent substrate, which is composed of an ink of a single kind, inks of different kinds, or combination of the inks, based on the spectral transmittances of the respective ink layers which have been precisely obtained based on the spectral reflection radiance factor free of an influence of the fluorescent substrate i.e. the fluorescent sample. Also, this arrangement enables to precisely obtain the bi-spectral luminescent radiance factor $F(\mu,\lambda)$ or the effective bi-spectral luminescent radiance factor $Fe(\mu,\lambda)$, as the effective excitation-fluorescence characteristics.

Further, the optical property measuring method is a method for estimatively calculating the spectral transmittance of the ink layer composed of an ink of a single kind, inks of different kinds, or combination of the inks, based on a measurement value of the spectral reflection radiance factor. The third step is a step of calculating the spectral transmittance $T(\lambda)$ of the ink layer by correcting the spectral transmittances $T0(\lambda)$ of the respective reference ink layers by using the spectral reflection radiance factor $R(\lambda)$ of the respective ink layers and the spectral reflection radiance factor $R0(\lambda)$ of the corresponding reference ink layer, based on the aforementioned Equation (36). By measuring and storing the spectral transmittance $T0(\lambda)$ and the spectral reflection radiance factor $R0(\lambda)$ of the corresponding reference ink layer, the spectral transmittance $T0(\lambda)$ of corresponding the ink layer can be precisely obtained based on the spectral reflection radiance factor $R0(\lambda)$ of the corresponding ink layer.

Further, the optical property measuring method is a method for estimatively calculating the spectral transmittance of the ink layer composed of an ink of a single kind, inks of different kinds, or combination of the inks, based on a measurement value of the spectral reflection radiance factor. The third step is a step of calculating the spectral transmittances $T(\lambda)$ of the respective ink layers based on a function of the spectral transmittances $T0(\lambda)$, $T1(\lambda)$, . . . and the spectral reflection radiance factors $R0(\lambda)$, $R1(\lambda)$, . . . of one or more reference ink layers having transmittances different from each other, with the spectral reflection radiance factor $R(\lambda)$ of the ink layer, for instance, based on the aforementioned Equation (36), or the following Equation (47) or (471).

In the above arrangement, the spectral transmittance $T(\lambda)$ of the ink layer is derived by the function of the spectral transmittances $T0(\lambda)$, $T1(\lambda)$, ... and the spectral reflection radiance factors $R0(\lambda)$, $R1(\lambda)$, ... of one or more reference ink layers having transmittances different from each other, with the spectral reflection radiance factor $R(\lambda)$ of the ink layer. By measuring and storing the spectral transmittances $T0(\lambda)$, $T1(\lambda)$, ... and the spectral reflection radiance factors $R0(\lambda)$, $R1(\lambda)$, ... of one or more reference ink layers having transmittances different from each other, the spectral transmittance $T(\lambda)$ of the corresponding ink layer can be precisely obtained based on the spectral reflection radiance factor $R(\lambda)$ of the corresponding ink layer.

The following modifications are applicable to the embodiment. (1) In the embodiment, each time measurement is performed, the spectral intensities $I1(\lambda)$ and $I2(\lambda)$ of sample illumination by the illuminations $I1$ and $I2$ are obtained based on the spectral intensities $Mx1(\lambda)$ and $Mx2(\lambda)$ of reference light, by using the conversion coefficients $D1(\lambda)$ and $D2(\lambda)$ based on the Equations (19) and (20), respectively. Alternatively, spectral intensities $I1(\lambda)$ and $I2(\lambda)$ of sample illumination at the time of white calibration may be used as the spectral intensities of sample illumination at the time of measurement. The spectral intensities $I1(\lambda)$ and $I2(\lambda)$ of sample illumination at the time of white calibration are obtained by the spectral intensities $Sw1(\lambda)$ and $Sw2(\lambda)$ of sample light obtained in illuminating the white calibration standard with the illuminations $I1$ and $I2$, the sensitivity calibration coefficient $G(\lambda)$ by the Equation (16), and the known reflection spectral radiance factor $Rw(\lambda)$, based on the following Equations (45) and (46), respectively.

$$I1(\lambda)=G(\lambda)/Rw(\lambda)\cdot Sw1(\lambda) \qquad (45)$$

$$I2(\lambda)=G(\lambda)/Rw(\lambda)\cdot Sw2(\lambda) \qquad (46)$$

In the above modified method, unlike the embodiment, the spectral intensities $I1(\lambda)$ and $I2(\lambda)$ of sample illumination are not used, each time measurement is performed. However, the modified method is advantageous because a reference optical system is not required, and an unduly large error may not occur, if the light sources of the first and the second illuminators are an incandescent lamp and an ultraviolet LED, and these light sources are stably operated in a short time corresponding to a time interval required in white calibration. Thus, the modified technology is applicable to an inexpensive measuring apparatus without a reference optical system.

(2) In the embodiment, the spectral transmittances $Ty(\lambda)$, $Tm(\lambda)$, and $Tc(\lambda)$ of the whole printed surfaces printed with the individual inks, or the spectral transmittances $Ty(\lambda)$, $Tm(\lambda)$, $Tc(\lambda)$, $Tym(\lambda)$, $Tmc(\lambda)$, $Tcy(\lambda)$, and $Tymc(\lambda)$ of the whole printed surfaces printed with the individual inks and combination of the inks under the same printing condition as the printed surface to be measured, are derived by using the spectral reflection radiance factor reference value $R0(\lambda)$ of the corresponding reference printed surface and the spectral reflection radiance factor $R(\lambda)$ of the corresponding whole printed surface, and by correcting the spectral transmittance reference value $T0(\lambda)$ of the corresponding reference printed surface based on the aforementioned Equation (39). Alternatively, these spectral transmittances may be derived by another Equation.

In the following, a modification of using another Equation is described. In the modification, a first reference printed surface and a second reference printed surface having ink layer thicknesses and/or ink concentrations different from each other are used, although the first reference printed surface and the second reference printed surfaces are both whole printed surfaces printed with the same ink. Assuming that the spectral transmittances of the first reference printed surface and the second reference printed surface are $T0y(\lambda)$ and $T1y(\lambda)$, and the spectral reflection radiance factors thereof are $R0y(\lambda)$ and $R1y(\lambda)$, the spectral transmittance $Ty(\lambda)$ of a whole printed surface having a spectral reflection radiance factor $Ry(\lambda)$ is derived from the following Equation (47).

$$Ty(\lambda)=Ay(\lambda)\cdot T0y(\lambda)+(1-Ay(\lambda))\cdot T1y(\lambda) \qquad (47)$$

where $Ay(\lambda)=((Ry(\lambda))^{1/2}-(R1y(\lambda))^{1/2})/((R0y(\lambda))^{1/2}-(R1y(\lambda))^{1/2})$ \qquad (471)

Specifically, the Equation (47) is expressed by synthesizing the spectral transmittances $T0y(\lambda)$ and $T1y(\lambda)$ of the first reference printed surface and the second reference printed surface with use of a weight. The weight is derived based on one-half squared differences between the spectral reflection radiance factor $Ry(\lambda)$ of the whole printed surface and the spectral reflection radiance factor $R1y(\lambda)$ of the second reference printed surface, and between the spectral reflection radiance factor $R0y(\lambda)$ of the first reference printed surface and the spectral reflection radiance factor $R1y(\lambda)$ of the second reference printed surface. Similarly to the embodiment, in the modification, in the wavelength region from 300 to 390 nm where there is no actual measurement value for $R0y(\lambda)$, $Ry1(\lambda)$ and $Ry(\lambda)$, $R0y(\mathbf{400})$, $R1y(\mathbf{400})$, and $Ry(\mathbf{400})$ where the wavelength $\lambda$ is 400 nm are used.

As described above, the optical property measuring method is a method for estimatively calculating the spectral transmittance of the ink layer composed of an ink of a single kind, inks of different kinds, or combination of the inks, based on a measurement value of the spectral reflection radiance factor. The third step is a step of calculating the spectral transmittances of the respective ink layers by correcting the spectral transmittances of at least two reference ink layers having transmittances different from each other, namely, the first reference ink layer and the second reference ink layer, or the first reference printed surface and the second reference printed surface, in other words, the spectral transmittance $T0(\lambda)$ of the first reference ink layer and the spectral transmittance $T1(\lambda)$ of the second reference ink layer, based on the Equation (47), in other words, based on the following Equation (47') concerning the individual inks and combination of the inks, by linear combination using a predetermined weighting factor $A(\lambda)$. In this arrangement, by measuring and storing the spectral transmittances $T0(\lambda)$, $T1(\lambda)$, and the spectral reflection radiance factors $R0(\lambda)$, $R1(\lambda)$ of at least two reference ink layers, the spectral transmittance $T(\lambda)$ of the corresponding ink layer can be precisely obtained based on the spectral reflection radiance factors of the respective ink layers. $A(\lambda)$ indicates a weighting factor to be derived based on the spectral reflection radiance factors $R0(\lambda)$ and $R1(\lambda)$ of the first reference ink layer and the second reference ink layer, and the spectral reflection radiance factor $R(\lambda)$ of the corresponding ink layer (see the Equation (471)).

$$T(\lambda)=A(\lambda)\cdot T0(\lambda)+(1-A(\lambda))\cdot T1(\lambda) \qquad (47')$$

The specification discloses the various arrangements as described above. The following is a summary of the main arrangements.

An optical property measuring method according to an aspect of the invention calculates a spectral transmittance characteristic of a colored layer on a substrate by using a spectral reflection characteristic of the colored layer. The method comprises: a first step of acquiring a reference spectral transmittance characteristic and a reference spectral reflection characteristic of a reference colored layer composed of a colorant in a predetermined condition; a second step of measuring a spectral reflection characteristic of the colored layer on the substrate; and a third step of correcting the reference spectral transmittance characteristic based on the reference spectral reflection characteristic and the spectral reflection characteristic to estimatively calculate a spectral transmittance characteristic of the colored layer.

Preferably, the optical property measuring method further comprises: a fourth step of estimatively calculating a bi-spectral characteristic of the colored layer on the substrate based on the estimatively calculated spectral transmittance characteristic and a known bi-spectral characteristic of the substrate.

Preferably, in the optical property measuring method, the substrate is a fluorescent substrate, and in the fourth step, a bi-spectral luminescent radiance factor of the colored layer on the substrate is calculated.

An optical property measuring method according to an aspect of the invention calculates a spectral transmittance characteristic of a colored layer composed of an ink of a single kind, inks of different kinds, or combination of the inks, by using a spectral reflection characteristic of the colored layer. The method comprises: a first step of acquiring a spectral transmittance characteristic and a spectral reflection characteristic of a reference colored layer defined as a reference, the reference colored layer being substantially identical or approximate to the colored layer; a second step of measuring a spectral reflection characteristic of the colored layer; and a third step of correcting the spectral transmittance characteristic of the reference colored layer based on the spectral reflection characteristic of the colored layer and the spectral reflection characteristic of the reference colored layer to calculate a spectral transmittance characteristic of the colored layer.

In the above arrangement, the optical property measuring method for calculating the spectral transmittance characteristic of the colored layer composed of the ink of the single kind, the inks of the different kinds, or the combination of the inks, by using the spectral reflection characteristic of the colored layer, comprises: the first step of acquiring the spectral transmittance characteristic and the spectral reflection characteristic of the reference colored layer defined as the reference, the reference colored layer being substantially identical or approximate to the colored layer; the second step of measuring the spectral reflection characteristic of the colored layer; and the third step of correcting the spectral transmittance characteristic of the reference colored layer based on the spectral reflection characteristic of the colored layer and the spectral reflection characteristic of the reference colored layer to calculate the spectral transmittance characteristic of the colored layer.

According to the optical property measuring method, the spectral transmittance characteristic of the colored layer is calculated by correcting the acquired spectral reflection characteristic of the reference colored layer based on the acquired spectral reflection characteristic of the reference colored layer and the measured spectral reflection characteristic of the colored layer. In other words, the spectral transmittance characteristic of the colored layer is estimated based on the acquired spectral transmittance characteristic of the reference colored layer, based on the acquired spectral reflection characteristic of the reference colored layer and the measured spectral reflection characteristic of the colored layer. This enables to obtain information on the spectral transmittance characteristic of the colored layer with sufficient precision in conformity with the printing condition of the printed sample to be measured. Specifically, even if the spectral transmittance characteristic of the colored layer is varied by a colored layer thickness difference or an ink concentration difference resulting from a difference in printing machine, ambient temperature or a like factor, the spectral transmittance characteristic of the colored layer can be precisely obtained. As a result, colorimetry of the printed color of the fluorescent sample i.e. the colored surface of the fluorescent substrate can be accurately performed by using the spectral transmittance characteristic of the colored layer.

In the optical property measuring method, preferably, the spectral transmittance characteristic includes a spectral transmittance characteristic in a measurable wavelength region where the spectral reflection characteristic is derived, and a non-measurable wavelength region where the spectral reflection characteristic is not derived, and the third step is a step of correcting the spectral transmittance characteristic of the reference colored layer based on the spectral reflection characteristics of the colored layer and the reference colored layer in the measurable wavelength region, if a wavelength to be measured is in the measurable wavelength region, and based on the spectral reflection characteristics of the colored layer and the reference colored layer in an adjacent wavelength region in the measurable wavelength region, the adjacent wavelength region being adjacent the non-measurable wavelength region, if the wavelength to be measured is in the non-measurable wavelength region.

In the above arrangement, the spectral transmittance characteristic includes the spectral transmittance characteristic in the measurable wavelength region where the spectral reflection characteristic is derived, and the non-measurable wavelength region where the spectral reflection characteristic is not derived. The third step is the step of correcting the spectral transmittance characteristic of the reference colored layer, based on the spectral reflection characteristics of the colored layer and the reference colored layer in the measurable wavelength region, if the wavelength to be measured is in the measurable wavelength region, and based on the spectral reflection characteristics of the colored layer and the reference colored layer in the adjacent wavelength region in the measurable wavelength region, the adjacent wavelength region being adjacent the non-measurable wavelength region, if the wavelength to be measured is in the non-measurable wavelength region.

According to the optical property measuring method, the spectral transmittance characteristic of the reference colored layer is corrected, based on the spectral reflection characteristics of the colored layer and the reference colored layer in the measurable wavelength region if the wavelength to be measured is in the measurable wavelength region, and based on the spectral reflection characteristics of the colored layer and the reference colored layer in the adjacent wavelength region, adjacent the non-measurable wavelength region, in the measurable wavelength region, if the wavelength to be measured is in the non-measurable wavelength region. In this arrangement, in correcting the spectral transmittance characteristic of the reference colored layer, the spectral reflection characteristic in the adjacent wavelength region in the measurable wavelength region where the spectral reflection characteristic is derived can be used for measurement in the non-measurable wavelength region where an actual measurement value of the spectral reflection characteristic is not derived. Thereby, the spectral transmittance characteristics of the respective reference ink layers in the measurable wavelength region and the non-measurable wavelength region can be easily corrected by using the spectral reflection characteristics of the colored layer and the reference colored layer.

In the optical property measuring method, preferably, the optical property measuring method is a method for calculating a spectral transmittance characteristic of a colored surface on a fluorescent substrate, the colored surface being composed of the colorant of a single kind, the colorants of different kinds, or combination of the colorants, and the third step is a step of calculating an average spectral transmittance characteristic of the colored surface, based on the spectral transmittance characteristic of the colored surface, and an area ratio of the colorant of the single kind, the colorants of the different kinds, or the combination of the colorants.

In the above arrangement, the optical property measuring method is the method for calculating the spectral transmittance characteristic of the colored surface on the fluorescent substrate. The colored surface is composed of the colorant of the single kind, the colorants of the different kinds, or combination of the colorants. The third step is the step of calculating the average spectral transmittance characteristic of the colored surface, based on the measured spectral transmittance characteristic of the colored surface, and the area ratio of the colorant of the single kind, the colorants of the different kinds, or the combination of the colorants.

According to the optical property measuring method, the average spectral transmittance characteristic of the colored surface is calculated based on the calculated spectral transmittance characteristic of the colored layer and the area ratio of the colorant of at least one or more kinds, or the combination of the colorants. In this arrangement, even if the spectral transmittance characteristic of the colored surface is varied by a colored layer thickness difference or an ink concentration difference resulting from a difference in printing machine, ambient temperature, or a like factor, the average spectral transmittance characteristic of the colored surface can be precisely obtained.

In the optical property measuring method, preferably, the optical property measuring method is a method for calculating excitation-fluorescence characteristics of the colored surface on the fluorescent substrate, and the method further comprises a step of calculating effective excitation-fluorescence characteristics of the colored surface based on the calculated average spectral transmittance characteristic and excitation-fluorescence characteristics of the fluorescent substrate.

In the above arrangement, the optical property measuring method is the method for calculating the excitation-fluorescence characteristics of the colored surface on the fluorescent substrate. The method further comprises the step of calculating the effective excitation-fluorescence characteristics of the colored surface based on the calculated average spectral transmittance characteristic and the excitation-fluorescence characteristics of the fluorescent substrate.

According to the optical property measuring method, the effective excitation-fluorescence characteristics of the colored surface are calculated based on the calculated average spectral transmittance characteristic and the excitation-fluorescence characteristics of the fluorescent substrate. Even if the spectral transmittance characteristic of the colored surface is varied by a colored layer thickness difference or an ink concentration difference resulting from a difference in printing machine, ambient temperature, or a like factor, the effective excitation-fluorescence characteristics of the colored surface can be precisely obtained.

In the optical property measuring method, preferably, the spectral transmittance characteristic is a spectral transmittance, and the spectral reflection characteristic is a spectral reflection radiance factor.

In the above arrangement, the spectral transmittance characteristic is the spectral transmittance, and the spectral reflection characteristic is the spectral reflection radiance factor.

According to the optical property measuring method, the spectral transmittance characteristic is the spectral transmittance, and the spectral reflection characteristic is the spectral reflection radiance factor. This enables to obtain the average spectral transmittance of the colored surface on the fluorescent substrate, which is composed of a colorant of a single kind or colorants of different kinds, based on the spectral transmittance, which has been precisely obtained based on the spectral reflection radiance factor free of an influence of the fluorescent substrate i.e. the fluorescent sample. This enables to precisely obtain a bi-spectral luminescent radiance factor or an effective bi-spectral luminescent radiance factor, as the effective excitation-fluorescence characteristics.

In the optical property measuring method, preferably, the optical property measuring method is a method for estimatively calculating the spectral transmittance of the colored layer composed of the colorant of a single kind, the colorants of different kinds, or combination of the colorants, based on a measurement value of the spectral reflection radiance factor, and the third step is a step of correcting the spectral transmittance of the reference colored layer by using the spectral reflection radiance factor of the colored layer and the reference spectral reflection radiance factor of the reference colored layer based on the following Equation (I) to calculate the spectral transmittance of the colored layer.

$$T(\lambda)=(R(\lambda)/R0(\lambda))^{1/2} \cdot T0(\lambda) \qquad (I)$$

where the symbol "/" indicates division, the symbol "·" indicates multiplication, $T(\lambda)$ indicates the spectral transmittance of the colored layer, $R(\lambda)$ indicates the spectral reflection radiance factor of the colored layer, $T0(\lambda)$ indicates the spectral transmittance of the reference colored layer, and $R0(\lambda)$ indicates the reference spectral reflection radiance factor of the reference colored layer.

In the above arrangement, the optical property measuring method is the method for estimatively calculating the spectral transmittance of the colored layer composed of the colorant of the single kind, the colorants of the different kinds, or the combination of the colorants, based on the measurement value of the spectral reflection radiance factor. The third step is the step of correcting the spectral transmittance of the reference colored layer by using the spectral reflection radiance factor of the colored layer and the reference spectral reflection radiance factor of the reference colored layer based on the Equation (I) to calculate the spectral transmittance of the colored layer.

According to the optical property measuring method, the spectral transmittance characteristic of the colored layer is calculated by correcting the reference spectral transmittance characteristic of the reference colored layer by using the spectral reflection radiance factor of the colored layer and the reference spectral reflection radiance factor of the reference colored layer. This enables to precisely obtain the spectral transmittance of the colored layer based on the spectral reflection radiance factor of the colored layer by measuring and storing the spectral transmittance and the reference spectral reflection radiance factor of the reference colored layer.

In the optical property measuring method, preferably, the optical property measuring method is a method for estimatively calculating the spectral transmittance of the colored layer composed of the colorant of a single kind, the colorants of different kinds, or combination of the colorants based on a measurement value of the spectral reflection radiance factor, and the third step is a step of correcting the reference spectral transmittances of at least a first reference colored layer and a second reference colored layer having transmittances different from each other by linear combination using a predetermined weighting factor based on the following Equation (II) to calculate the spectral transmittance of the colored layer.

$$T(\lambda)=A(\lambda)\cdot T0(\lambda)+(1-A(\lambda))\cdot T1(\lambda) \qquad (II)$$

where the symbol indicates "·" multiplication, $T(\lambda)$ indicates the spectral transmittance of the colored layer, $T0(\lambda)$ indicates the spectral transmittance of the first reference colored layer, $T1(\lambda)$ indicates the spectral transmittance of the second reference colored layer, and $A(\lambda)$ indicates a weighting factor to be derived based on the reference spectral reflection radiance factor $R0(\lambda)$ of the first reference colored layer and the reference spectral reflection radiance factor $R1(\lambda)$ of the second reference colored layer, and the spectral reflection radiance factor $R(\lambda)$ of the colored layer.

In the above arrangement, the optical property measuring method is the method for estimatively calculating the spectral transmittance of the colored layer composed of the colorant of the single kind, the colorants of the different kinds, or the combination of the colorants based on the measurement value of the spectral reflection radiance factor. The third step is the step of correcting the reference spectral transmittances of at least the first reference colored layer and the second reference colored layer having the transmittances different from each other by the linear combination using the predetermined weighting factor based on the Equation (II) to calculate the spectral transmittance of the colored layer.

According to the optical property measuring method, the spectral transmittance of the colored layer is calculated by correcting the reference spectral transmittances of at least the two reference colored layers having the transmittances different from each other, i.e., the first reference colored layer and the second reference colored layer, based on the Equation (II), with use of the linear combination using the predetermined weighting factor. This enables to precisely obtain the spectral transmittance of the colored layer based on the spectral reflection radiance factor of the colored layer by measuring and storing the reference spectral transmittances and the reference spectral reflection radiance factors of at least the two reference colored layers.

In the optical property measuring method, preferably, the optical property measuring method is a method for estimatively calculating the spectral transmittance of the colored layer composed of the colorant of a single kind, the colorants of different kinds, or combination of the colorants based on a measurement value of the spectral reflection radiance factor, and the third step is a step of deriving the spectral transmittance of the colored layer by a function of the reference spectral transmittances and the reference spectral reflection radiance factors of one or more reference colored layers having transmittances different from each other with the spectral reflection radiance factor of the colored layer.

In the above arrangement, the optical property measuring method is the method for estimatively calculating the spectral transmittance of the colored layer composed of the colorant of the single kind, the colorants of different kinds, or the combination of the colorants based on the measurement value of the spectral reflection radiance factor. The third step is the step of deriving the spectral transmittance of the colored layer by the function of the reference spectral transmittances and the reference spectral reflection radiance factors of the one or more reference colored layers having the transmittances different from each other with the spectral reflection radiance factor of the colored layer.

According to the optical property measuring method, the spectral transmittance of the colored layer is derived by the function of the reference spectral transmittances and the reference spectral reflection radiance factors of the one or more reference colored layers having the transmittances different from each other with the spectral reflection radiance factor of the colored layer. This enables to precisely obtain the spectral transmittance of the colored layer based on the spectral reflection radiance factor of the colored layer by measuring and storing the reference spectral transmittances and the reference spectral reflection radiance factors of the one or more reference colored layers having the transmittances different from each other.

An optical property measuring apparatus according to another aspect of the invention calculates a spectral transmittance characteristic of a colored layer on a substrate by using a spectral reflection characteristic of the colored layer. The apparatus comprises: a storing section for acquiring and storing a reference spectral transmittance characteristic and a reference spectral reflection characteristic of a reference colored layer composed of a colorant in a predetermined condition; a measuring section for measuring a spectral reflection characteristic of the colored layer on the substrate; and an estimative calculating section for correcting the reference spectral transmittance characteristic based on the reference spectral reflection characteristic and the spectral reflection characteristic to estimatively calculate a spectral transmittance characteristic of the colored layer.

Preferably, the estimative calculating section estimatively calculates a bi-spectral characteristic of the colored layer on the substrate based on the estimatively calculated spectral transmittance characteristic and a known bi-spectral characteristic of the substrate.

Preferably, in the case where the substrate is a fluorescent substrate, the estimative calculating section estimatively calculates a bi-spectral luminescent radiance factor of the colored layer on the fluorescent substrate based on the estimatively calculated spectral transmittance characteristic and a known bi-spectral characteristic of the fluorescent substrate.

An optical property measuring apparatus according to another aspect of the invention calculates a spectral transmittance characteristic of a colored layer composed of a colorant of a single kind, colorants of different kinds, or combination of the colorants, by using a spectral reflection characteristic of the colored layer. The apparatus comprises: a storing section for storing a spectral transmittance characteristic and a spectral reflection characteristic of a reference colored layer defined as a reference, the reference colored layer being substantially identical or approximate to the colored layer; a measuring section for measuring a spectral reflection characteristic of the colored layer; and a correcting section for correcting the spectral transmittance characteristic of the reference colored layer based on the spectral reflection characteristic of the colored layer and the spectral reflection characteristic of the reference colored layer to calculate a spectral transmittance characteristic of the colored layer.

In the above arrangement, the optical property measuring apparatus for calculating the spectral transmittance characteristic of the colored layer composed of the colorant of the single kind, the colorants of the different kinds, or the combination of the colorants, by using the spectral reflection characteristic of the colored layer, comprises: the storing section for storing the spectral transmittance characteristic and the spectral reflection characteristic of the reference colored layer defined as the reference, the reference colored layer being substantially identical or approximate to the colored layer; the measuring section for measuring the spectral reflection characteristic of the colored layer; and the correcting section for correcting the spectral transmittance characteristic of the reference colored layer based on the spectral reflection characteristic of the colored layer and the spectral reflection characteristic of the reference colored layer to calculate the spectral transmittance characteristic of the colored layer.

According to the optical property measuring apparatus, the spectral transmittance characteristic of the colored layer is calculated by correcting the acquired spectral transmittance characteristic of the reference colored layer, based on the acquired spectral reflection characteristic of the reference colored layer and the measured spectral reflection characteristic of the colored layer. In other words, the spectral transmittance characteristic of the colored layer is estimated based on the acquired spectral transmittance characteristic of the reference colored layer, based on the acquired spectral reflection characteristic of the reference colored layer and the measured spectral reflection characteristic of the colored layer. This enables to obtain information on the spectral transmittance characteristic of the colored layer with sufficient precision in conformity with the printing condition of the printed sample to be measured. Specifically, even if the spectral transmittance characteristic of the colored layer is varied by a colored layer thickness difference or an ink concentration difference resulting from a difference in printing machine, ambient temperature or a like factor, the spectral transmittance characteristic of the colored layer can be precisely obtained. As a result, colorimetry of the printed color of the fluorescent sample i.e. the colored surface on the fluorescent substrate can be accurately performed by using the spectral transmittance characteristic of the colored layer.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An optical property measuring method for calculating a spectral transmittance characteristic of a colored layer on a substrate by using a spectral reflection characteristic of the colored layer, the method comprising:
    a first step of acquiring a reference spectral transmittance characteristic and a reference spectral reflection characteristic of a reference colored layer composed of a colorant in a predetermined condition;
    a second step of measuring a spectral reflection characteristic of the colored layer on the substrate; and
    a third step of correcting the reference spectral transmittance characteristic based on the reference spectral reflection characteristic and the spectral reflection characteristic to estimatively calculate a spectral transmittance characteristic of the colored layer.

2. The optical property measuring method according to claim 1, further comprising:
    a fourth step of estimatively calculating a bi-spectral characteristic of the colored layer on the substrate based on the estimatively calculated spectral transmittance characteristic and a known bi-spectral characteristic of the substrate.

3. The optical property measuring method according to claim 2, wherein
    the substrate is a fluorescent substrate, and in the fourth step, a bi-spectral luminescent radiance factor of the colored layer on the substrate is calculated.

4. The optical property measuring method according to claim 1, wherein
    the optical property measuring method is a method for calculating a spectral transmittance characteristic of a colored surface on a fluorescent substrate, the colored surface being composed of the colorant of a single kind, the colorants of different kinds, or combination of the colorants, and
    the third step is a step of calculating an average spectral transmittance characteristic of the colored surface, based on the spectral transmittance characteristic of the colored surface, and an area ratio of the colorant of the single kind, the colorants of the different kinds, or the combination of the colorants.

5. The optical property measuring method according to claim 4, wherein
    the optical property measuring method is a method for calculating excitation-fluorescence characteristics of the colored surface on the fluorescent substrate, and
    the method further comprises a fifth step of calculating effective excitation-fluorescence characteristics of the colored surface based on the calculated average spectral transmittance characteristic and excitation-fluorescence characteristics of the fluorescent substrate.

6. The optical property measuring method according to claim 1, wherein
    the spectral transmittance characteristic is a spectral transmittance, and the spectral reflection characteristic is a spectral reflection radiance factor.

7. The optical property measuring method according to claim 6, wherein
    the optical property measuring method is a method for estimatively calculating the spectral transmittance of the colored layer composed of the colorant of a single kind, the colorants of different kinds, or combination of the colorants, based on a measurement value of the spectral reflection radiance factor, and
    the third step is a step of correcting the reference spectral transmittance of the reference colored layer by using the spectral reflection radiance factor of the colored layer and the reference spectral reflection radiance factor of the reference colored layer based on the following Equation (I) to calculate the spectral transmittance of the colored layer $$T(\lambda) = (R(\lambda)/R0(\lambda))^{1/2} \cdot T0(\lambda) \qquad (I)$$

where the symbol "/" indicates division,
    the symbol "·" indicates multiplication,
    $T(\lambda)$ indicates the spectral transmittance of the colored layer,
    $R(\lambda)$ indicates the spectral reflection radiance factor of the colored layer, T0(λ) indicates the reference spectral transmittance of the reference colored layer, and R0(λ) indicates the reference spectral reflection radiance factor of the reference colored layer.

8. The optical property measuring method according to claim 6, wherein the optical property measuring method is a method for estimatively calculating the spectral transmittance of the colored layer composed of the colorant of a single kind, the colorants of different kinds, or combination of the colorants based on a measurement value of the spectral reflection radiance factor, and the third step is a step of correcting the reference spectral transmittances of at least a first reference colored layer and a second reference colored layer having transmittances different from each other by linear combination using a predetermined weighting factor based on the following Equation (II) to calculate the spectral transmittance of the colored layer $$T(\lambda) = A(\lambda) \cdot T0(\lambda) + (1 - A(\lambda)) \cdot T1(\lambda) \quad (II)$$

where the symbol "·" indicates multiplication,

T(λ) indicates the spectral transmittance of the colored layer,

T0(λ) indicates the reference spectral transmittance of the first reference colored layer, T1(λ) indicates the reference spectral transmittance of the second reference colored layer, and A(λ) indicates a weighting factor to be derived based on the reference spectral reflection radiance factor R0(λ) of the first reference colored layer and the reference spectral reflection radiance factor R1(λ) of the second reference colored layer, and the spectral reflection radiance factor R(λ) of the colored layer.

9. The optical property measuring method according to claim 6, wherein the optical property measuring method is a method for estimatively calculating the spectral transmittance of the colored layer composed of the colorant of a single kind, the colorants of different kinds, or combination of the colorants based on a measurement value of the spectral reflection radiance factor, and the third step is a step of deriving the spectral transmittance of the colored layer by a function of the reference spectral transmittances and the reference spectral reflection radiance factors of one or more reference colored layers having transmittances different from each other with the spectral reflection radiance factor of the colored layer.

10. The optical property measuring method according to claim 1, wherein the spectral transmittance characteristic includes a spectral transmittance characteristic in a measurable wavelength region where the spectral reflection characteristic is derived, and a non-measurable wavelength region where the spectral reflection characteristic is not derived, and the third step is a step of correcting the reference spectral transmittance characteristic based on the spectral reflection characteristic and the reference spectral reflection characteristic in the measurable wavelength region, if a wavelength to be measured is in the measurable wavelength region, and based on the spectral reflection characteristic and the reference spectral reflection characteristic in an adjacent wavelength region in the measurable wavelength region, the adjacent wavelength region being adjacent the non-measurable wavelength region, if the wavelength to be measured is in the non-measurable wavelength region.

11. An optical property measuring apparatus for calculating a spectral transmittance characteristic of a colored layer on a substrate by using a spectral reflection characteristic of the colored layer, the apparatus comprising:

a storing section for acquiring and storing a reference spectral transmittance characteristic and a reference spectral reflection characteristic of a reference colored layer composed of a colorant in a predetermined condition;

a measuring section for measuring a spectral reflection characteristic of the colored layer on the substrate; and an estimative calculating section for correcting the reference spectral transmittance characteristic based on the reference spectral reflection characteristic and the spectral reflection characteristic to estimatively calculate a spectral transmittance characteristic of the colored layer.

12. The optical property measuring apparatus according to claim 11, wherein the estimative calculating section estimatively calculates a bi-spectral characteristic of the colored layer on the substrate based on the estimatively calculated spectral transmittance characteristic and a known bi-spectral characteristic of the substrate.

13. The optical property measuring apparatus according to claim 11, wherein in the case where the substrate is a fluorescent substrate, the estimative calculating section estimatively calculates a bi-spectral luminescent radiance factor of the colored layer on the fluorescent substrate based on the estimatively calculated spectral transmittance characteristic and a known bi-spectral characteristic of the fluorescent substrate.

* * * * *